US009788731B2

United States Patent
Parmar et al.

(10) Patent No.: US 9,788,731 B2
(45) Date of Patent: Oct. 17, 2017

(54) OPTICAL ENDOLUMINAL FAR-FIELD MICROSCOPIC IMAGING CATHETER

(75) Inventors: Jaywant Philip Parmar, Morro Bay, CA (US); Richard W. Mead, Los Altos Hills, CA (US); Matthew David Fate, Boulder Creek, CA (US)

(73) Assignee: Jaywant Philip Parmar, San Louis Obispo, CA (US)

( * ) Notice: Subject to any disclaimer, the term of this patent is extended or adjusted under 35 U.S.C. 154(b) by 596 days.

(21) Appl. No.: 13/401,676

(22) Filed: Feb. 21, 2012

(65) Prior Publication Data

US 2012/0212595 A1    Aug. 23, 2012

Related U.S. Application Data

(60) Provisional application No. 61/444,898, filed on Feb. 21, 2011.

(51) Int. Cl.
*A61B 6/00* (2006.01)
*A61B 5/00* (2006.01)
(Continued)

(52) U.S. Cl.
CPC .......... *A61B 5/0084* (2013.01); *A61B 1/0011* (2013.01); *A61B 1/0017* (2013.01);
(Continued)

(58) Field of Classification Search
CPC .................................................. A61B 5/0084
(Continued)

(56) References Cited

U.S. PATENT DOCUMENTS 3,818,902 A * 6/1974 Kinoshita .......... A61B 1/00096
385/118
5,344,419 A * 9/1994 Spears ............................ 606/15
(Continued)

FOREIGN PATENT DOCUMENTS

WO    WO 2010077626 A1 * 7/2010 ............. G21K 1/025
WO    WO 2010103718 A1 * 9/2010
(Continued)

OTHER PUBLICATIONS

WO2010137375A1 translation.*
WO2010103718A1 translation.*

*Primary Examiner* — Jennifer Dieterle
*Assistant Examiner* — Lisa Kinnard
(74) *Attorney, Agent, or Firm* — Michael D. Eisenberg

(57) ABSTRACT

An optical endoluminal far-field microscopic imaging catheter comprises a light generating system, a first light delivery conduit for propagating light generated by the light generating system and a light distributor configured to redirect light propagated by the delivery conduit into a direction of an object to be imaged. A discriminator is configured for capturing light reflected from the object incident on a window of the discriminator from a particular direction and transmitting only the light captured from the particular direction to a second light delivery conduit. A drive mechanism is configured to sweep the window through a plurality of directions in a predictable pattern for matching each light capture event in the window with a direction of the window during the event. An analyzer matches the direction of the window with an associated light capture event and generate a visible image based on a mosaic of the captured light.

16 Claims, 17 Drawing Sheets

(51) Int. Cl.
*A61B 1/00* (2006.01)
*A61B 1/04* (2006.01)
*A61B 1/07* (2006.01)

(52) U.S. Cl.
CPC ...... *A61B 1/00177* (2013.01); *A61B 1/00179* (2013.01); *A61B 1/043* (2013.01); *A61B 1/07* (2013.01); *A61B 5/0062* (2013.01); *A61B 5/0066* (2013.01); *A61B 5/6852* (2013.01)

(58) Field of Classification Search
USPC ...................................................... 600/478
See application file for complete search history.

(56) References Cited

U.S. PATENT DOCUMENTS

| | | | | |
|---|---|---|---|---|
| 5,603,687 | A * | 2/1997 | Hori | A61B 1/00096 348/45 |
| 6,046,868 | A * | 4/2000 | Theriault | G01N 21/15 359/196.1 |
| 6,052,613 | A * | 4/2000 | Takaki | A61B 5/02154 600/479 |
| 6,794,656 | B2 * | 9/2004 | Francke et al. | 250/385.1 |
| 7,019,309 | B2 * | 3/2006 | Gu | G02B 23/26 250/458.1 |
| 7,286,222 | B2 * | 10/2007 | Gardner, Jr. | G01J 3/02 356/244 |
| 8,258,532 | B2 * | 9/2012 | Van Gorkom et al. | 257/98 |
| 2003/0071194 | A1 * | 4/2003 | Mueller | G01B 11/00 250/208.1 |
| 2003/0130562 | A1 * | 7/2003 | Barbato et al. | 600/109 |
| 2004/0184758 | A1 * | 9/2004 | Liu | G02B 6/327 385/147 |
| 2005/0161589 | A1 * | 7/2005 | Kim | B82Y 20/00 250/216 |
| 2005/0215873 | A1 * | 9/2005 | Peter | A61B 5/0059 600/407 |
| 2005/0219674 | A1 * | 10/2005 | Asai | G02B 26/0833 359/213.1 |
| 2006/0058614 | A1 * | 3/2006 | Tsujita | A61B 8/12 600/407 |
| 2007/0187580 | A1 * | 8/2007 | Kykta | H04N 9/3129 250/227.15 |
| 2008/0228086 | A1 * | 9/2008 | Ilegbusi | A61B 5/0066 600/479 |
| 2008/0287783 | A1 * | 11/2008 | Anderson | 600/429 |
| 2009/0018393 | A1 * | 1/2009 | Dick | A61B 5/0062 600/109 |
| 2009/0069743 | A1 * | 3/2009 | Krishnamoorthy et al. | 604/66 |
| 2010/0047733 | A1 * | 2/2010 | Nahlieli | 433/29 |
| 2010/0122355 | A1 * | 5/2010 | Paragas et al. | 800/3 |
| 2010/0125165 | A1 * | 5/2010 | Torii et al. | 600/106 |
| 2010/0143192 | A1 * | 6/2010 | Myrick et al. | 422/45 |
| 2010/0198316 | A1 * | 8/2010 | Toselli et al. | 607/88 |

FOREIGN PATENT DOCUMENTS

| | | | | |
|---|---|---|---|---|
| WO | WO 2010128605 | A1 * | 11/2010 | ......... A61B 1/00147 |
| WO | WO 2010137375 | A1 * | 12/2010 | |

* cited by examiner

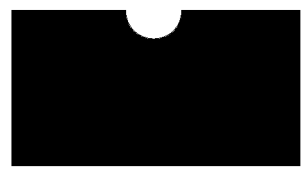
Fig. 16

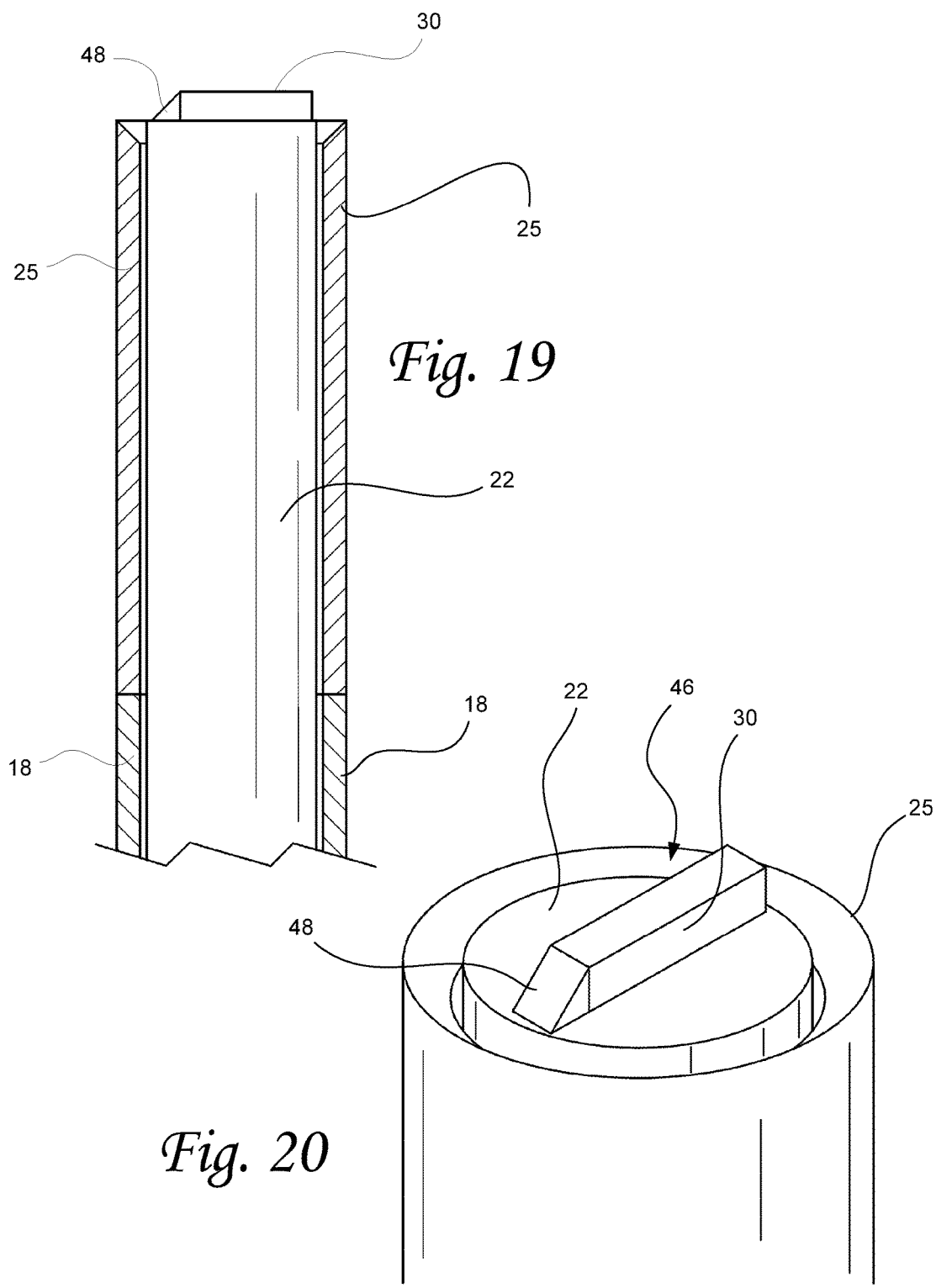

2100

```
A ROD OR SLAB OF SCHOTT
OPTICAL GLASS, DESIGNATION F2
(OR EQUIVALENT) IS CUT,
GROUND, AND POLISHED INTO A
45/45/90 DEGREE TRIANGULAR
CROSS-SECTION, MEASURING
APPROXIMATELY 25 INCHES ON A
SIDE. 2105
```

↓

```
THE PRISM PREFORM IS DRAWN
DOWN TO A TARGET SIZE OF
0.12MM ON A SIDE 2110
```

↓

```
THE DRAWN MATERIAL IS DICED
1715 INTO SEGMENTS
MEASURING APPROXIMATELY
0.12MM LONG, PRODUCING
PRISMS WITH 0.12 X ~0.12 MM
INPUT AND OUTPUT FACES 2115
```

*Fig. 21*

OPTICAL ENDOLUMINAL FAR-FIELD MICROSCOPIC IMAGING CATHETER

CROSS-REFERENCES TO RELATED APPLICATIONS

The present application claims priority from U.S. Provisional Application Ser. No. 61/444,898 filed on Feb. 21, 2011, which is hereby incorporated herein by reference in its entirety.

TECHNICAL FIELD

The present invention, in some embodiments thereof, relates to endoluminal imaging devices, and some particular embodiments related to a catheter based, far field, visible light based single pixel cameral imaging device.

BACKGROUND OF THE INVENTION

Stroke is a leading cause of morbidity and mortality in aging western populations. The causes of stroke are multiple, with most falling into a category of "cryptogenic" etiology. Most of these cryptogenic events are felt to be related to atheroma at the carotid bifurcation and atheroembolus to the ipsilateral cerebral hemisphere. There is much pathological evidence to support this supposition; however, clearly definitive evidence of the hypothesis will never be essentially achievable at the present limits of imaging technology due to the physical limitations of current, state-of-the-art nondestructive anatomical imaging.

Carotid atheroma is nonetheless felt to be the most important source of stroke. Historically, removing a risky plaque through surgical carotid Endarterectomy has been proven to improve outcomes via a randomized controlled trial: the NASCET. In this historical study, the risk due to plaque was determined by the finding of lumenographic severe stenosis and proxy markers for this angiographic finding. Thus, an imaging based, somewhat subjective medical assessment of lumenographic severe stenosis (70-99% narrowed) is currently the mainstay logic behind the medical decision to proceed with or withhold the only proven surgical treatment for the culprit atherosclerotic lesion: carotid endarterectomy. The patients identified with severe stenosis are either symptomatic (having a history of TIA/stroke) or asymptomatic from their carotid bifurcation plaque, and surgical decision making has evolved to incorporate this data into the clinical decision making risk model. The goal of this procedure of endarterectomy is to excise the dangerous atheroma at the carotid bifurcation safely.

Lumenographic imaging has significant limitations. Via these methods, the blood pool within a vessel is imaged and the thickness and geometry of the vessel wall is inferred/imagined by an imaging expert. The finding of "severe stenosis" has become the driving logic behind this imaging technique. The mathematical definition of this term is imprecise and based ultimately on a subjective interpretation of where the vessel adventitial surface lies (the extreme outer wall of the vessel, or, anatomically what is known as the vascular adventitial layer). The thickening of the vessel wall, from outermost adventitia to innermost endothelium is inferred from the geometry of the lumen. Stenosis is best and most widely understood as the geometrical narrowing of a 2-d projection of the blood pool transversely to the axis of the vascular flow vector.

Patients with 60-69% stenosis who are symptomatic may be offered additional antiplatelet adhesion medications which are felt, on aggregate, to reduce their risks for further events.

Concurrently developing with the previously described surgical and medical decision model, a model atherosclerosis lesion progression and regression has been developed in part by the American Heart Association based on histopathology and cadaver studies. The model is inherently based on destructive pathological imaging, thus, it is inherently limited in its extent of application. This model identifies the Type VI plaque as one that is directly associated with atheroembolism. By definition, this type of plaque displays "disruption of the lesion surface, hematoma or hemorrhage, and thrombotic deposits." Circulation. 1995; 92:1355-1374 doi: 10.1161/01.CIR.92.5.1355 (Circulation. 1995; 92:1355-1374.)® 1995 American Heart Association, Inc. A Definition of Advanced Types of Atherosclerotic Lesions and a Histological Classification of Atherosclerosis—A Report From the Committee on Vascular Lesions of the Council on Arteriosclerosis, American Heart Association. Herbert C. Stary, MD, CHAIR; A. Bleakley Chandler, MD; Robert E. Dinsmore, MD; Valentin Fuster, MD, PhD; Seymour Glagov, MD; William Insull, Jr, MD; Michael E. Rosenfeld, PhD; Colin J. Schwartz, MD; William D. Wagner, PhD; Robert W. Wissler, PhD, MD.

Conceivably, these three markers would be optically visible from the lumen of the vessel if the blood pool was cleared of blood transiently and an optical scope was to effectively sample the region of the carotid bifurcation using traditional reflected light anatomical-optical data as well as transilluminated anatomical-optical data and with sufficient detail. These images could secure the diagnosis of Type VI atheroma independent of the presence of stenosis. This would provide a logical and clinically applicable manner in which to medically assess the risk of stroke due to vulnerable or active atherosclerotic disease. If there is a surface tear, ulcer, thrombus in situ, and/or hemorrhage into the wall of the vessel, the plaque is unstable and is capable of throwing a clot downstream to the brain at any time. This is specifically the very valuable clinical information that this device will provide.

Imaging based enterprises to blend the pathologically based models to nondestructive imaging based models of discrete atherosclerotic lesions have been ongoing and present an opportunity to better understand and treat carotid atheroma. The carotid bifurcation presents a uniquely patterned region for atheroma development and risk.

Atherosclerosis is a systemic disease affecting the entire arterial vascular system. The device will allow study of this specific disease in a number of locations where the disease may be present, including the coronary arteries, renal arteries, splanchnic arteries and extremity arteries.

Additional optical imaging study of the carotid bifurcation and other endovascular positions could be performed with the catheter using fluorescent optical probes that are designed to bind to cell surface receptors, cell surface molecules and extracellular materials that are important to disease such as fibrin or platelet aggregates. Through excitation of the marker probe fluorescence and detection and spatial localization of the fluorescence, sophisticated and nondestructive in-situ study of atherosclerosis will be enabled by the catheter.

Furthermore, the immediate benefits to society of better carotid bifurcation atherosclerotic disease characterization and the of monitoring of progression/regression of these critical atherosclerotic lesions will be great as medical treatments such as blood thinners of various design and endovascular plaque stabilization treatments such as stents and drug eluting balloon angioplasty are offered to patients with critical disease that was previously completely unrecognized.

In broader applications, optical imaging in the manner outlined above may inform research and development into a number of diseases including but not limited to Parkinson's disease, Alzheimer's disease and Multiple Sclerosis. In these three examples, the catheter assembly would be inserted directly into the brain tissue similarly to other electrodes and ventricular catheters that are surgically inserted through the brain tissue. Optical fluorescent marker molecular probes could be directly applied to the interstitial fluid of the brain via catheter sideholes, through the cerebrospinal fluid via lumbar or dural puncture, or, through the vascular system using a standard intravenous injection. The data obtained through nondestructive in-situ evaluation using molecular probes could lead to a better understanding of these disease processes. Currently, there is little robust pathophysiological information regarding the pathophysiology of these disease processes due to the inability to study the disease in vivo in humans at cellular and molecular levels of detail. The device is designed to enable these studies.

However, the immediate specific aim of the present invention is to identify and characterize critical disease at the carotid bifurcation in a clinically effective manner using technology that is currently enabled.

BRIEF SUMMARY OF EMBODIMENTS OF THE INVENTION

The present invention relates to an imaging device based on optical detection of reflected visible light in its most elementary form, and, IR light and/or excited fluorescent light in some embodiments.

(1) An aspect of some embodiments to the present invention relates to an imaging system, comprising: a light generating system; a light delivery conduit for propagating light generated by the light generating system; a light distributor configured to redirect light propagated by the delivery conduit into a direction of an object to be imaged; a directional light discriminator configured for capturing light reflected from the object incident on a window of the discriminator from a particular direction and transmitting only the light captured from the particular direction to the light delivery conduit; a drive mechanism coupled to the window, configured to sweep the window through a plurality of directions in a predictable pattern for matching each light capture event in the window with a direction of the window during the event; and an optical to electrical conversion module for converting an optional signal corresponding to an light capture event into an electrical signal capable of being reconstructed into a visible image.

(2) In a variant, the imaging system is configured for deployment in interior body regions. The imaging system comprises a catheter tube, wherein the light delivery conduit, the directional light discriminator and the light distributor are disposed inside the catheter tube and are configured to operate inside the catheter tube for imaging interior body regions.

(3) In another variant of the imaging system, the directional light discriminator comprises a single pixel camera.

(4) In a further variant of the imaging system, the directional light discriminator comprises a channel formed of translucent material.

(5) In still another variant, the directional light discriminator is configured having a geometric design that permits the passage of light through the discriminator only traveling from within an acceptance region in front of the discriminator determined by the geometry of the discriminator.

(6) In yet a further variant of the imaging system, the directional light discriminator comprises a rotatable lens assembly. The lens assembly comprises a transparent channel surrounded by and held in place by a light absorbing material.

(7) In another variant, the directional light discriminator comprises a selective window. The selective window comprises: a transparent core having a first refractive index; a transparent cladding around the transparent core having a second refractive index; and an opaque housing around the cladding. The second refractive index is between 0.001 and 0.030 less than the first refractive or is between 0.001 and 0.030 greater than the first refractive index.

(8) In a further variant, the imaging system comprises an optical light tube configured to receive a rotating optical light guide through a central bore. The optical light tube has channels distributed within a periphery of the optical light tube configured for receiving the light delivery conduit. The optical light tube is configured to translate in a linear direction while maintaining a fixed rotational position.

(9) In still another variant, the drive mechanism is configured to translate the directional light discriminator in a linear direction and rotate the directional light discriminator 360 degrees, allowing the directional light discriminator to capture reflected light emitted from the light distributor and reflected off an object being imaged or capture induced fluorescently generated light, induced by illumination of light channeled by the distributor to the surface being imaged.

(10) In yet a further variant, the light generating system comprises a laser for generating laser light and the light distributor comprises a light diffuser configured to combine light from one or more lasers and uniformly illuminate a region of space in front of the diffuser. The diffuser is connected to a fiber optic light delivery conduit connected to the laser.

(11) In another variant, the imaging system comprise a fiber optic rotary adaptor (FORA) comprising a rotor end and a stator end. The FORA is connected downstream of the directional light discriminator, and the directional light discriminator is connected to the rotor end of the FORA via a rotating fiber optic light guide. The FORA is connected to the optical to electrical conversion module via a fiber optic light guide connected to the stator end.

(12) In a further variant, the imaging system comprises a light separator connected downstream of the directional light discriminator. Captured light from the directional light discriminator is divided into component light distinguished by wavelength by the light separator for processing by an analyzer.

(13) In still another variant, the imaging system comprises an analyzer coupled to the light delivery conduit, configured to match the direction of the window with an associated light capture event and generate a visible image based on a mosaic of the captured light.

(14) In yet a further variant, the drive mechanism is configured to spin the directional light discriminator during light capture events. The analyzer comprises a processor operable to reconstruct an image from reflected light data received from the directional light discriminator, by performing a reconstruction process comprising: receiving rotation speed data of the directional light discriminator; receiving light capture event rate data; assigning a pixel value based on a signal generated by the light capture event; assigning a first set of consecutive pixels to a first linear array based on the rotation speed data and the light capture event rate data; assigning a second set of consecutive pixels to a second linear array adjacent to the first linear array based on the rotation speed data and the light capture event rate data; and repeating the steps of assigning consecutive pixels to subsequent linear arrays based on the rotation speed data and the light capture event rate data.

(15) In a variant, the drive mechanism is configured to output an index signal to the processor at a constant point during each revolution of the directional light discriminator. The processor is operable to: assign the index signal to a pixel having a pixel value obtained from a light capture event occurring concurrently with the index signal; and perform a check of the start pixels of the linear arrays with the pixels having assigned index signals.

(16) In another variant, the light distributor is disposed adjacent the directional light discriminator and the light distributor is configured to rotate in synchronicity with the directional light discriminator and illuminate the space in front both components.

(17) In a further variant, the directional light discriminator comprises a nanoscale slit array.

(18) In still another variant, an imaging system comprises: a light generating system configured to generate a beam of light; a spinning first light delivery conduit for propagating light generated by the light generating system; an optical collimating tube connected to the light delivery conduit configured to reduce the width of the beam; a light detector disposed adjacent to the capillary optical collimating tube configured to capture light reflected from an object incident on the detector and transmitting the light captured to a second light delivery conduit; and a drive mechanism coupled to the spinning first light delivery conduit, configured to spin and simultaneously translate the first light delivery conduit and the capillary optical collimating tube in a linear direction in a predictable pattern for matching each light capture event in the detector with a direction of the capillary optical collimating tube during the event.

(19) In yet a further variant, a catheter based imaging system is configured for deployment in interior body regions. The catheter based imaging system comprises: a catheter tube; a laser; a first light guide for propagating light generated by the laser; an optical light tube configured to receive the first light guide in a perimeter section of the light tube and having an channel configured to receive a rotating second light guide while not rotating; a light diffuser connected to the first light guide, configured to uniformly distribute the light generated by the laser, and translate in a linear direction through the catheter tube; a rotatable lens assembly, comprising a transparent channel surrounded by and held in place by a light absorbing material, the rotatable lens assembly configured translate in a linear direction in sync with the light diffuser; a rotatable second light guide connected to the rotatable lens assembly; and a drive mechanism connected to the rotatable second light guide, and configured to sweep the lens assembly through a plurality of directions within the catheter in a predictable pattern for matching each light capture event in the transparent channel with a direction of the lens during the event. The drive mechanism is configured to translate the lens assembly in a linear direction and rotate the lens assembly. The drive mechanism is configured to translate the light diffuser in a linear direction through the catheter tube. The imaging system comprises: a light distributor configured to redirect light propagated by the delivery conduit into a direction of an object to be imaged; a directional light discriminator configured for capturing light reflected from the object incident on a window of the discriminator from a particular direction and transmitting only the light captured from the particular direction to the light delivery conduit; an optical to electrical conversion module for converting an optional signal corresponding to an light capture event into an electrical signal capable of being reconstructed into a visible image; and an analyzer coupled to the light delivery conduit, configured to match the direction of the window with an associated light capture event and generate a visible image based on a mosaic of the captured light.

(20) In a variant, the catheter based imaging system comprises a fiber optic rotary adaptor (FORA) comprising a rotor end and a stator end. The FORA is connected downstream of the lens assembly, wherein the lens assembly is connected to the rotor end of the FORA via the rotating light guide. The FORA is connected to the analyzer via a light guide connected to the stator end. The optical to electrical conversion module comprises a photomultiplier tube.

(21) In another variant, a method for imaging an object in an interior space comprises: positioning an optical light guide in front of the object in the interior space; pointing a narrow detector window at the object; illuminating the object by injecting illumination light into the light guide; collimating reflected light from the object to allow only light reflected off the object from one angle, through the detector; continuously spinning the narrow detector window with a predictable rotational speed, and a translating the detector in a linear direction at a predictable linear speed while the object is being illuminated for capturing and collimating reflected light from the object to allow only light reflected at about 90 degrees through the detector; and analyzing the detected light from the detector to reconstruct an image of the object.

(22) In a further variant of the method of imaging an object, the object is a vessel inner wall in an interior body space, and the method further comprises maneuvering the optical light guide and the detector inside a catheter tube to vicinity of the object.

(23) In still another variant of the method of imaging an object, illuminating the object comprises illuminating the object by injecting illumination light into a non-rotating the light guide.

(24) In yet a further variant, the method of imaging an object comprises spinning the detector via an attached spinning fiber optic light guide and transmitting the detected light through the spinning fiber optic light guide.

(25) In a variant, the method of imaging an object comprises: transmitting the reflected light from the spinning fiber optic cable to a non-rotating fiber optic cable; and converting the reflected light transmitted through the rotating fiber optic cable into an electrical signal for analysis to reconstruct an image of the object.

(26) In another variant of the method of imaging an object, the angle of the reflected light is about 0 degrees.

In some embodiments of the lens, nanoscale diffraction gratings are utilized as directional light discriminators, or, optical illumination beam focusing mechanisms.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 10 is a diagram illustrating the acceptance angles of light entering a lens window of diameter o and width a.

FIG. 16 is a diagram of lens during an intermediate stage of a lens manufacturing process;

FIG. 19 is a partial sectional view of optical imaging components disposed in a catheter tip of the imaging system;

FIG. 20 is a perspective detail view of optical imaging components disposed in a catheter tip of the imaging system;

FIG. 21 is a flow chart of a process for manufacturing a reflecting prism.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Definitions

Before describing aspects of the present invention, it is necessary to define terms that will be used in the current application.

The phrase "endovascular positioning" generally means placement of a device within soft tissues of the body or within veins or arteries and includes, but is not limited to the biliary system.

OCT is an abbreviation for optical coherence tomography, which is a developing technique that uses near-infrared light for the cross-sectional visualization of a vessel wall at the microscopic level.

ID and OD are abbreviations for inner diameter and outer diameter respectively.

The Z direction refers to linear movement along the length of the catheter.

NA refers to Numerical Aperture, a dimensionless number that characterizes the range of angles over which the system can accept or emit light.

PMT refers to photo multiplier tube.

CPU refers to a processor or central processing unit.

PID controller refers to a proportional-integral-derivative controller.

ADC refers to analogue to digital converter.

WDM refers to a wavelength division multiplexer.

FORA refers to a fiber optic rotary adapter.

FORJ refers to a fiber optic rotary joint.

CMOS array refers to Complementary metal-oxide-semiconductor imaging array.

o refers to the diameter of the lens window.

a refers to the length of the lens window.

RPS refers to revolutions per second.

Overview

Figure 1:
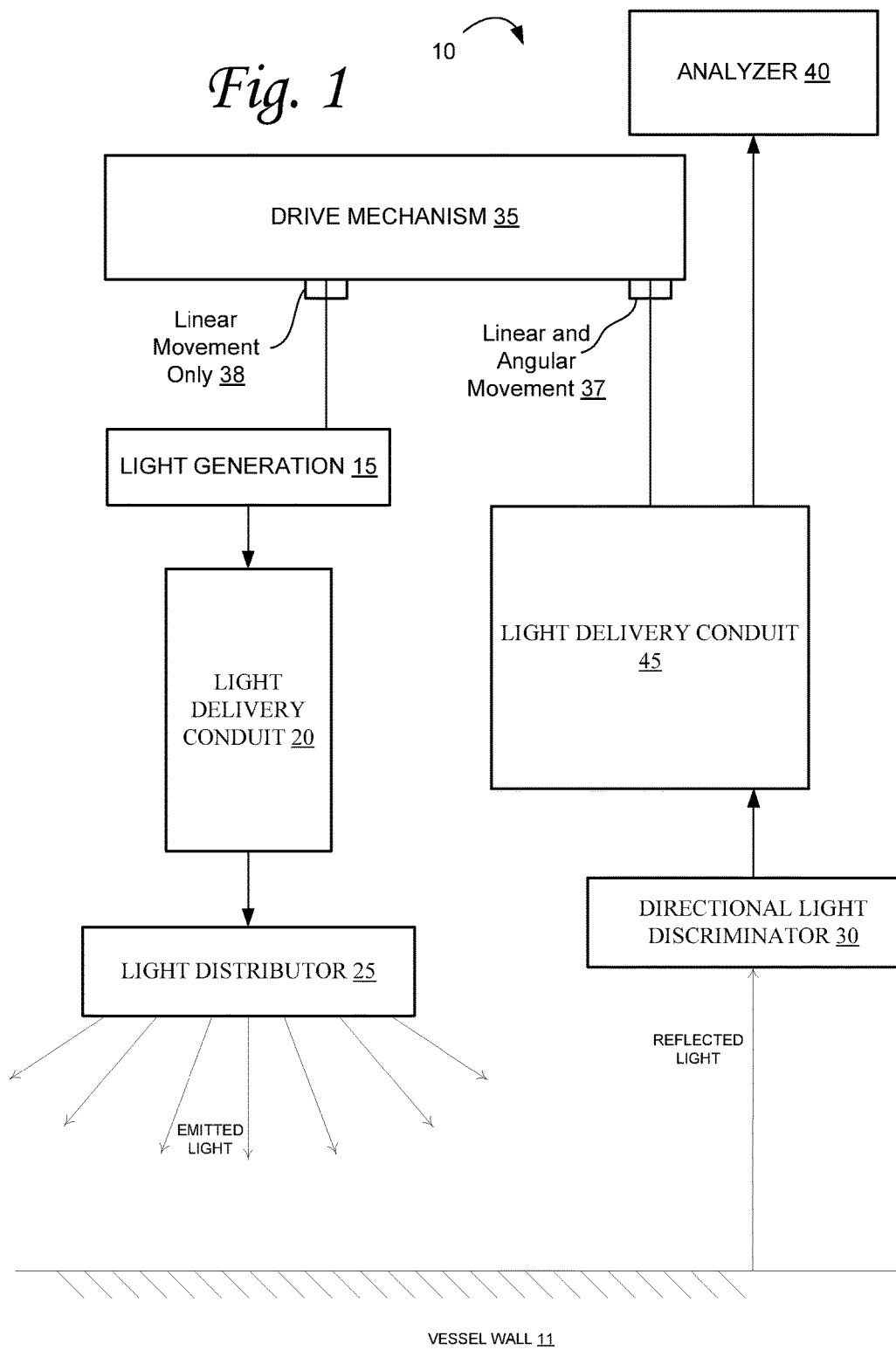
FIG. 1 is block diagram illustrating an imaging system in accordance with the principles of the invention.
Figure 4:
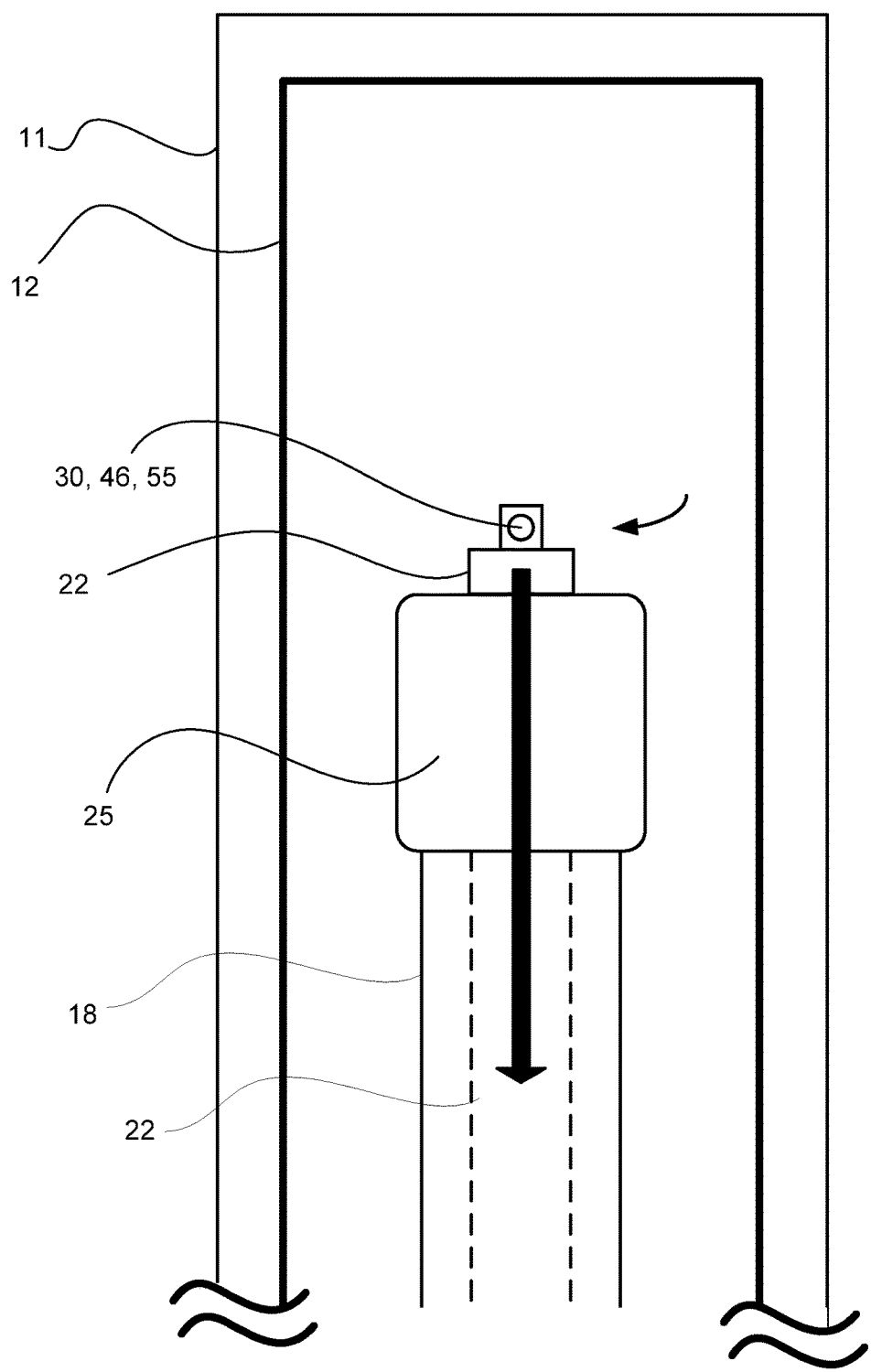
FIG. 4 is a conceptual diagram of the operation of the imaging system.

An aspect of some embodiments of the present invention relates to an imaging system 10 for imaging the interior wall 11 of a blood vessel, the lumen of the biliary or gastrointestinal tract, or the direct cellular and connective tissue structure of organs within a human body. The imaging system effectively operates as a single pixel fiber optic camera. A single pixel camera is necessarily a computational camera, relying on computerized data acquisition and rendering of these data. There are certain advantages of these data sets, notably including reconstruction techniques incorporating other sorts of computational datasets such as those derived from computed tomography or optical coherence tomography. FIGS. 1 and 4 illustrate the operation of the lens system within the lumen of a vessel being imaged. FIG. 4 is a conceptual illustration that depicts a lens window 55 disproportionately large and not to scale with the other depicted items in the illustration. A lens system located in a catheter 12 tip rotates around the Z axis, which may, although not necessarily, coincide with the center-line of a vessel to be imaged. As it rotates 360 degrees, the lens system continuously acquires image samples of the vessel wall. The lens system simultaneously moves linearly along the center-line as it rotates. The combined rotational and axial linear motion of the lens system enables the imaging system to assemble a mosaic of small reflected light samples to form an image of the vessel's inner facing wall.

The imaging system of the present invention incorporates a single pixel imaging system, such as the one described above, by mounting the system near the tip of a catheter 12. The light generated by the system for imaging is carried via a flexible fiber optic cable. The reflected light from the vessel wall absorbed by the imaging system is carried back to a detector via a fiber optic cable 45. The fiber optic cable itself is encased in the catheter, which can be modified to operate in any arterial, venous, endolumenal or internal tissue position which interventional radiologists, interventional cardiologists and surgeons are familiar with.

The imaging system incorporates a digital design for computerized data acquisition into the engineering of the device in order to achieve the high bandwidth data stream that is required for single pixel field scanning at high temporal and spatial resolution.

Variants of the imaging system have electronic linear and rotary actuators and encoders located ex-vivo and coupled to the sterile and endolumenal catheter via a single fiber optic waveguide of diameter 1000-1500 microns and length of 0.3-1.5 meters that transmits a single channel of optical frequency and amplitude data that is sensed from the catheter viewpoint. In this manner, appropriately selected digital actuators and encoders may form part of the system. Some variants may include motors and/or optical actuators located at the catheter tip that allow for the generation of forward or sideways directed viewpoints generated through aim and trajectory guidance of a directional light discriminator or array of directional light discriminators.

In a variant, referring to FIG. 1, the imaging system 10 comprises a light generating system 15. The light generating system is connected to a light delivery conduit for propagating light generated by the light generating system 20. The light delivery conduit delivers the generated light to a light distributor 25 that is configured to redirect light propagated by the delivery conduit into a direction of an object to be imaged. The light distributor 25 is configured to have its position adjusted in a linear direction. A directional light discriminator 30, or optionally an array of directional light discriminators, is configured for capturing light reflected from the object that impinges incident on a window of the discriminator from a particular direction and transmits only the light captured from the particular direction to the light delivery conduit. A drive mechanism 35 is coupled 37 to the window and the light distributor, and is configured to sweep the window through a plurality of directions and positions in a predictable pattern for matching each light capture event in the window with a direction of the window during the event.

Figure 5:
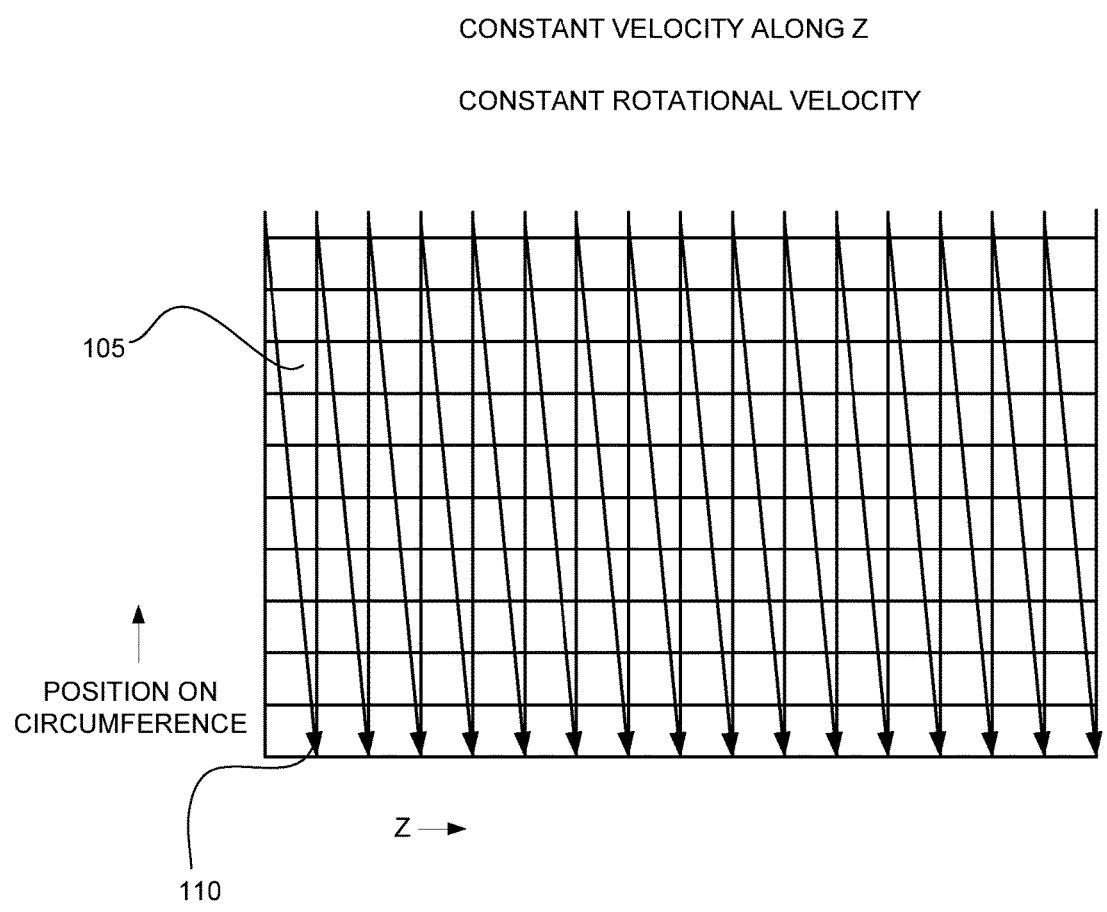
FIG. 5 is a conceptual diagram of a 2D reconstruction grid illustrating the relationship of the movement of a lens window through space and pixel data acquisition.

In one embodiment, referring to FIG. 4, the drive mechanism 35 is configured 37 to predictably rotate the light discriminator window and adjust the linear position of the light discriminator 30 parallel to its axis of rotation. The drive mechanism 35 is also configured 38 to adjust the position of the light distributor 25 in the same linear direction and in sync with the light discriminator 30. An analyzer 40 is coupled to the light delivery conduit and is configured to match the direction of the window with an associated light capture event and generate a visible image based on a mosaic of the captured light, as illustrated in FIG. 5.

Examples

In another variant of the present invention, the system comprises an endovascular, endoscopic catheter 12 or instrument mounted far field scanning optical microscope system. The imaging system is swept through a field of view in order to construct a large field of view perspective image from the catheter 12. A variety of optical scanning orbits can be utilized to generate an image, however most clinical embodiments are configured to conduct a spiral sweep of the optical sampling lens along the length of a catheter in order to generate an image of the vessel wall which is located at some distance from the catheter.

In the above variant, the microscopic imaging system is engineered to be miniaturized and placed into soft tissues of the body or within veins, arteries and the biliary system. The system goal is to obtain anatomical information using light. Illumination is provided by an illumination system that in most embodiments is constructed in parallel to an objective lens system.

Figure 2:
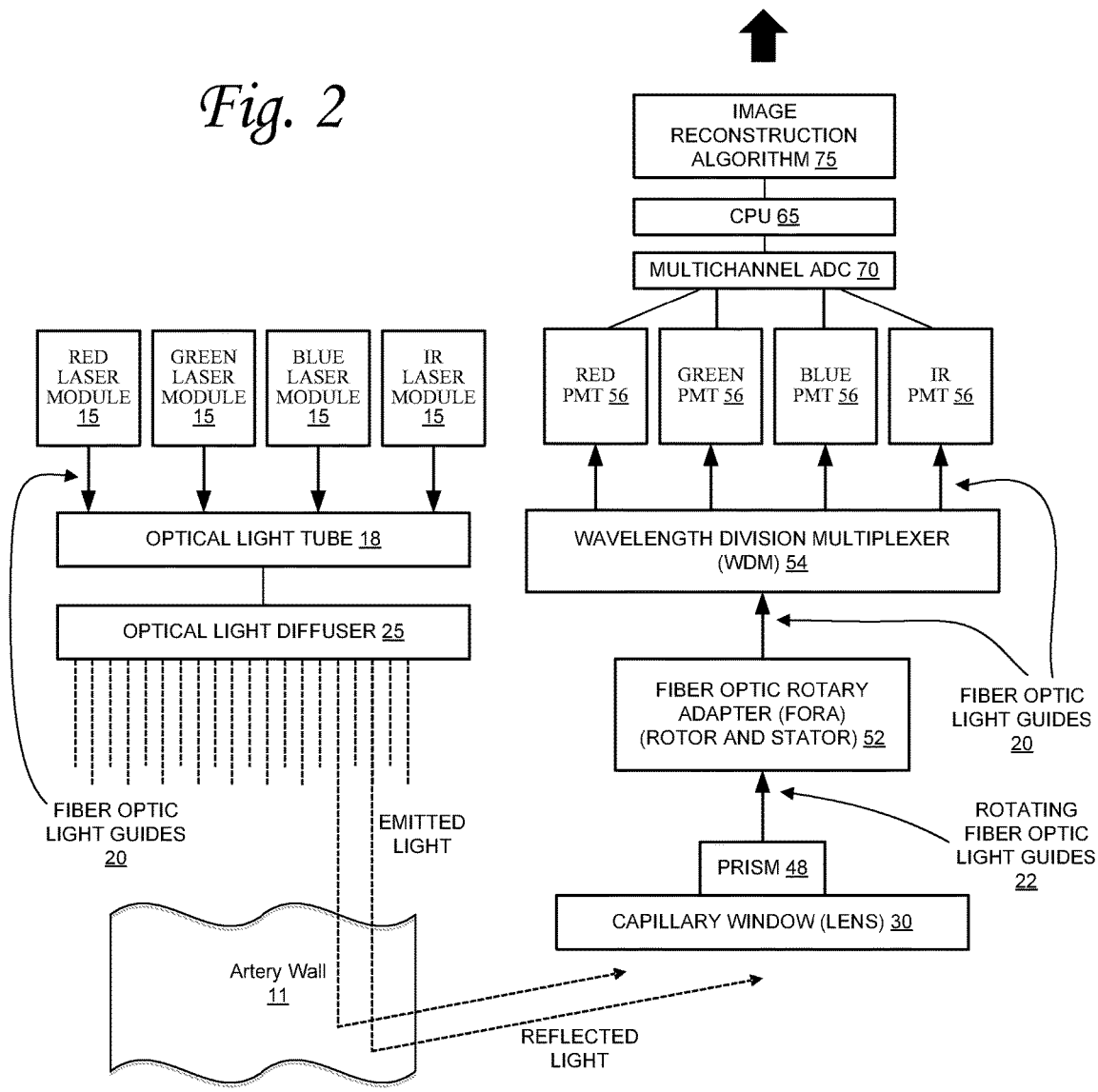
FIG. 2 is another block diagram illustrating a variant of the imaging system.
Figure 3:
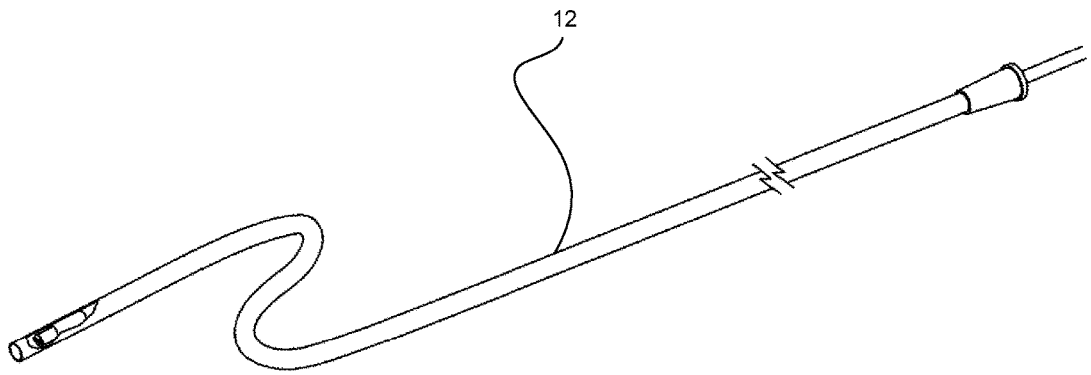
FIG. 3 is a perspective view of the imaging system embodied in a catheter environment.

In another variant, referring to FIG. 2, the system comprises a preferred light generating system 15 comprising distinct red, green, blue and IR laser modules 15. Optionally the light may be blended into a single beam. Optionally, the light generating system 15 is housed in a non-sterile and external cabinet that is optically and mechanically coupled to the sterile and translating and rotating lens. In some embodiments, the light generating system 15 is comprised of a white light laser system that generates a range of coherent wavelengths. In still another embodiment, the light generating system 15 comprises an integrating sphere assembly with an illumination source such as an incandescent or fluorescent lighting system and an output that is coupled to the catheter tip. Optionally, in cases where fluorescence imaging is desired, single or multiple laser or narrow pass filtered light around the target probe's fluorescence wavelength is included in the illumination beam.

Figure 8:
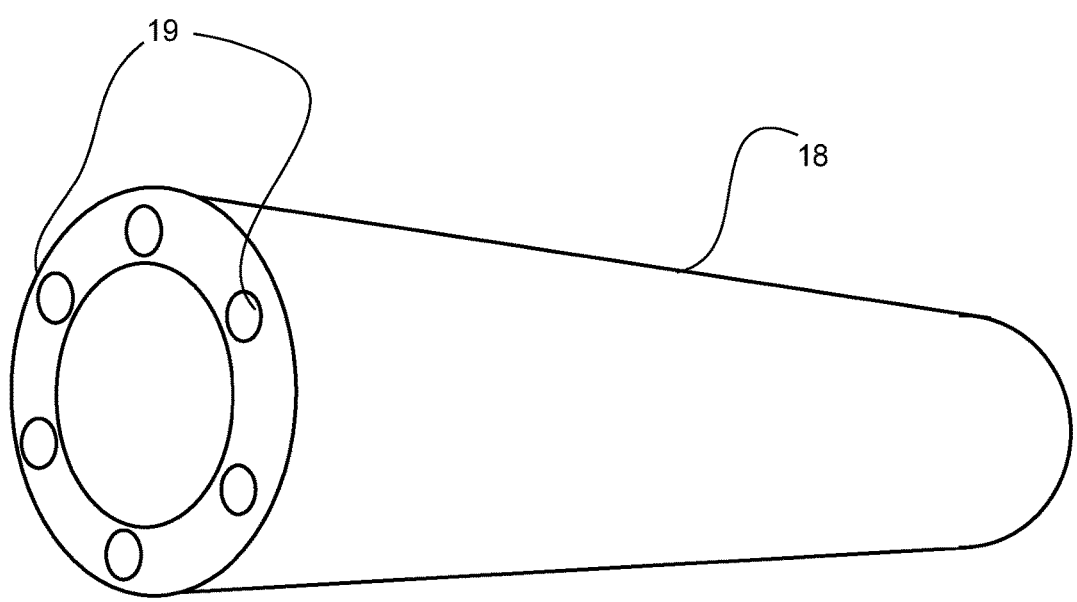
FIG. 8 is a perspective view of an optical light tube.

Generated laser light from the lasers 15 is channeled to a single or multiple fiber optic light guides 20 that are flexible and are placed into the body of the imaging catheter, into a portion of the catheter that translates in the Z direction with the focal plane of the directional light discriminator. In some embodiments, the illumination fiber 20 rotates with the directional light discriminator. In the case of multiple illumination fibers, referring to FIGS. 8 and 11, an optional optical light tube 18 is configured as a hollow cylinder with channels 19 distributed around the central axis of the light tube 18. In a variant, the optical light tube 18 is moveable within the catheter only in a linear direction along the Z direction of the catheter 12. The optical light tube 18 and any components carried by light tube are driven only in the Z direction by virtue of its mechanical connection to a drive mechanism 35. In one example, bushings disposed between the light tube 18 and the rotating optical fiber 22 maintain the rotational independence of the two components 18, 22.

Figure 11:
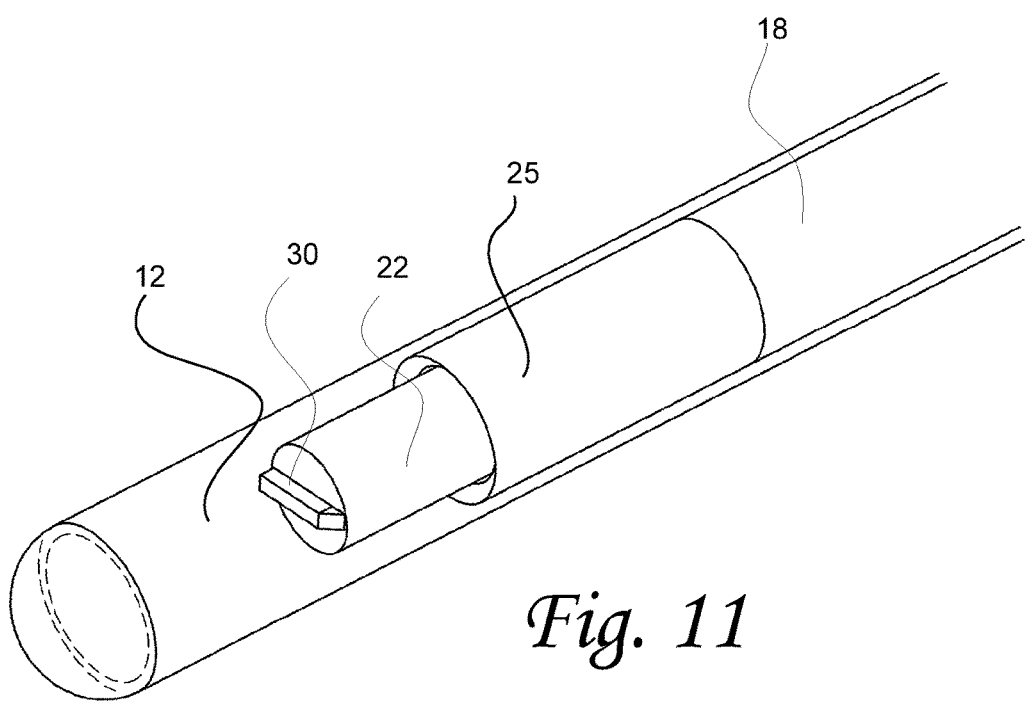
FIG. 11 is a perspective view of a catheter based imaging system with some of the imaging components disposed in a catheter tip.

In a further variant, referring to FIGS. 11 and 18-20, the light distributor 25 comprises an optical light diffuser assembly 25. The light diffuser assembly 25 may abut an edge of the cylindrical optical light tube 18, for being translated linearly by the optical light tube 18. FIG. 11 illustrates the rotating optical fiber 22 extended further beyond the diffuser than is necessary. This is for illustrative purposes and does not show optimal operating conditions. The fiber optic light guides 20 connected to the lasers 15 lead to the optical light diffuser assembly, configured to mix laser light to achieve a uniform illumination zone directed perpendicularly or at some angle relative to a window of a rotating directional light discriminator 30. In general, 10-20 times the input fiber diameter would be required in length of the diffuser guide in order to provide adequate mixing of the input light within the diffuser, so as to provide uniform illumination. The light is focused as efficiently as possible onto a single point of the object being imaged that follows the trajectory of the single pixel camera, or to a ring that traces or follows the trajectory of the catheter lens assembly. In some embodiments, the diffuser may be segmented into fiber optic waveguides so as to allow sequential illumination of independent segments around the circumference of the annulus. When the diffuser is operated as a collector, this would potentially increase the signal to noise ratio of the collector through minimization of secondary and higher order reflected light (signal) via a method of directional discrimination.

The diffuser 25 may be constructed by drawing a glass tube of an appropriate ID/OD combination so that the reduced (post-draw) size meets the ID/OD requirements of the catheter structure. It is desirable to match the surface area of its input surface to the output surface. This minimizes the angle through which the exiting light is sent, and, the numerical aperture of the system. It is desirable that NA×surface area at input equal NA×surface area of output. For example, if the output surface is smaller than the input, the output beam will be more dispersive. In an embodiment where the diffuser comprises a ring array of fibers, the illumination beam is naturally more dispersive than the input. An ideal situation would be a continuous annulus of optically conductive material that is flexible enough to allow catheter flexibility. This allows for a more optically focused illumination beam through conservation of NA with surface area. In some embodiments, coherent laser light may allow for a more collimated output despite decreases in the output surface area relative to the input surface area. In one embodiment, the distal end of the diffuser has an overall length from 5 mm to 10 mm and may be beveled (on its interior edge) and polished to a 40 to 50 degree angle, producing an annulus which reflects light injected into its polished proximal annular end outward and onto an interior vessel surface. The distal end may be fabricated from several types of glass. Some embodiments of the diffuser are configured to operate in air wherein the index of refraction of most glasses is sufficient to achieve the reflection.

In some embodiments, the illuminating light, or some portion of the illuminating light, may be carried by an objective data gathering light circuit. In these embodiments, the properties of optical coherence may be utilized to obtain adjunctive optical coherence tomographic data via methods that are well known by those versed in this technique. The OCT data may be used to calculate the distance from the objective lens to optical interfaces and to provide tissue characterization using the techniques of OCT image generation. The OCT data may be utilized to generate perspective/depth renderings of the reflected optical image data.

In some embodiments, rotational and possibly linear motion control of the imaging tip discriminator is obtained using a fixed magnet or electromagnet incorporated into the rotating tip. A rotational moment at the tip is generated using an external magnetic stator built into a gantry that encloses a space including the imaging tip and its embedded magnet. This technique would obviate portions of the direct mechanical coupling of the catheter to the catheter drive mechanism. In most of these designs, a miniature fiberoptic rotating joint would be placed at the catheter tip.

In some embodiments, pulsed DC electromagnetic tracking elements may be added to the catheter imaging tip in order to provide real time 3D localization of the catheter imaging tip position in space. This position/orientation data could be utilized by the analyzer to aid in generation of an image. The 3D tracking techniques that may apply to this device are well known to those versed in the art.

Example Lens Assemblies

After is light is emitted by the light distributor 25 or light diffuser 25, the light impinges upon a vessel surface and is reflected back to the directional light discriminator 30. Only light incident on the directional light discriminator at angles close to being perpendicular or 90 degrees to a window of the discriminator will pass into the light delivery conduit 45, by virtue of the configuration of the system 10.

In a variant, the light discriminator comprises a lens 30. A broad range of focal length of the lens is desirable in order to have ideal imaging characteristics for the purpose of medical imaging. In a variant, referring to FIGS. 9-12, the lens 30 is constructed in the form of an optical collimating tube with characteristics of far field sensitivity generally described as an acceptance cone that is defined by the length to diameter characteristics of the optical collimating tube. The tube itself may be constructed in a variety of manners. The lens 30 sits atop a lens assembly 46, comprising a rotating light guide or rotor-fiber 22, a prism and the lens. The lens assembly is configured to rotate a sufficient to obtain reflected light data within seconds. The lens may rotate anywhere from 40 RPS to 3000 RPS. In one variant, the lens rotates from 300-400 RPS.

Figure 9:
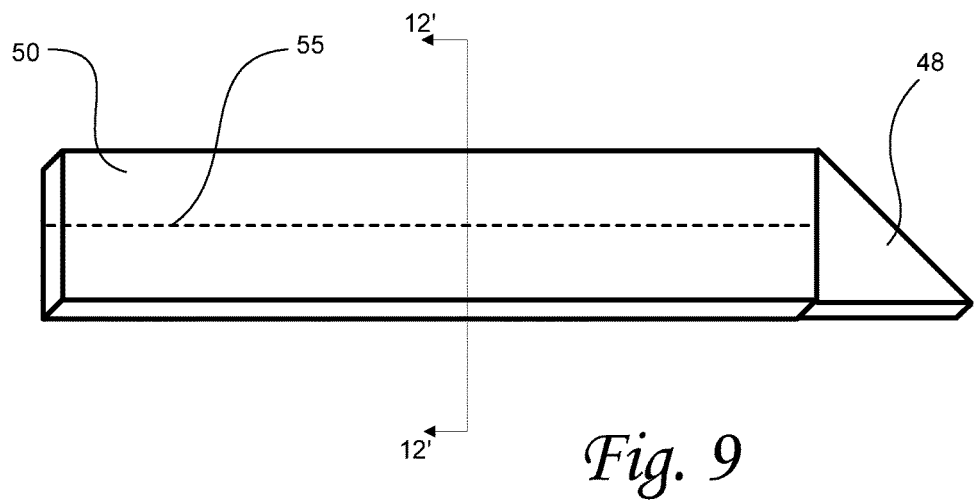
FIG. 9 is a diagram of a lens assembly.
Figure 10:
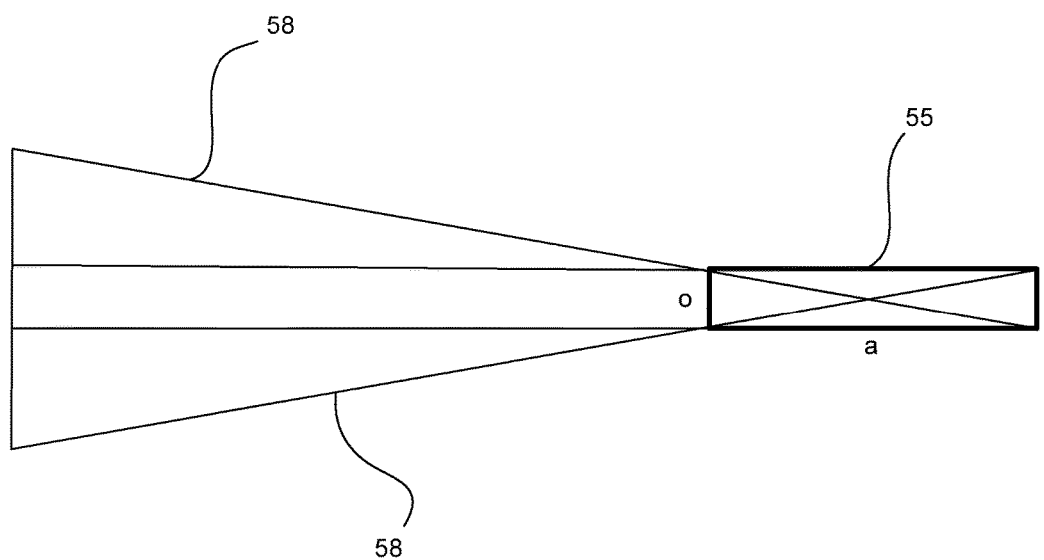
Figure 12:
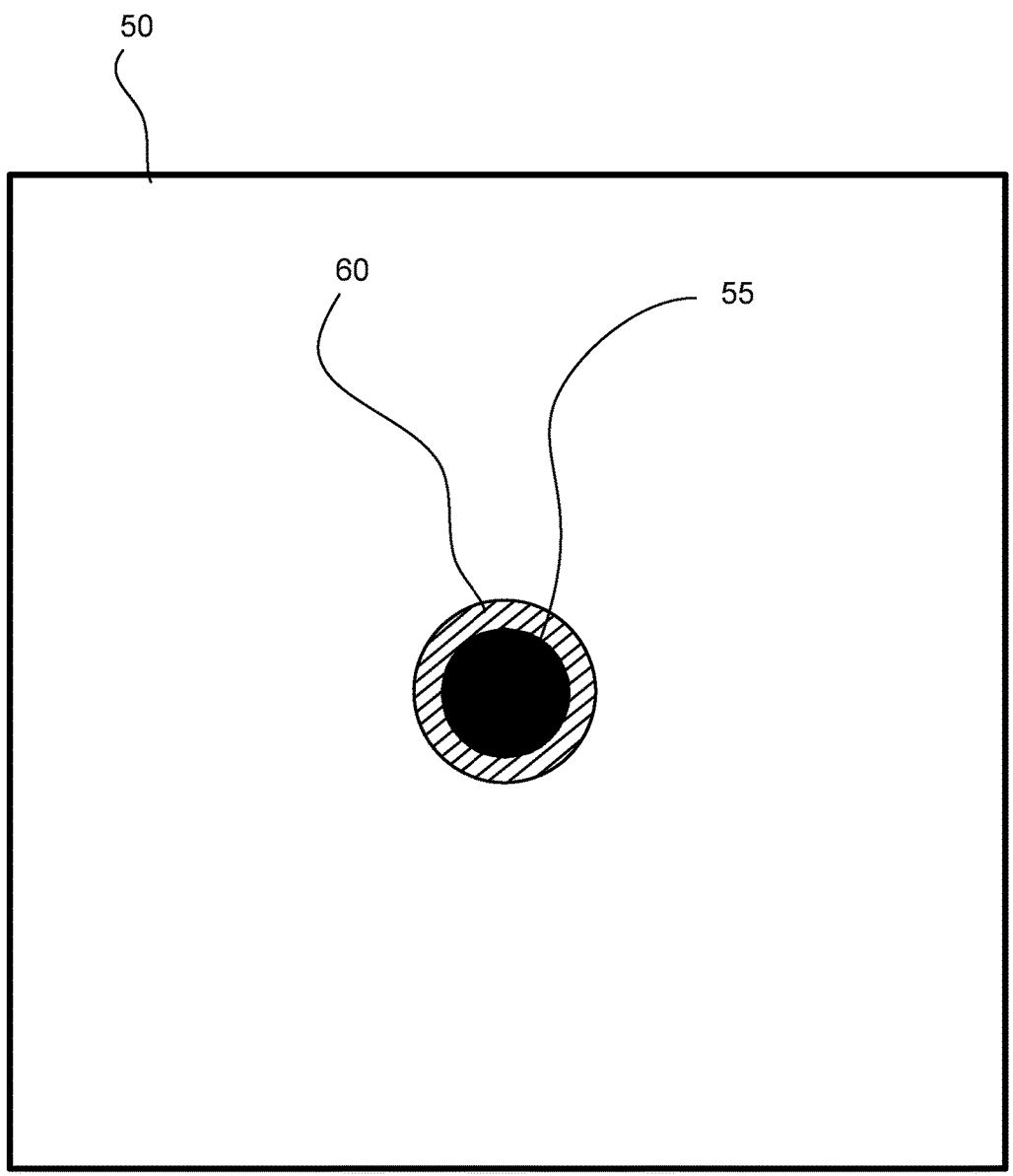
FIG. 12 is a conceptual diagram illustrating a cross section of a lens.

Referring to FIGS. 9, 10 and 12, in one embodiment the lens 30 comprises a fiber optic composite having a solid, black and totally absorptive bulk glass 50 that holds a totally transparent window 55. The window leads to and is the front face of a long capillary shaped light tube. Surrounding the window is a relatively thin layer cladding glass 60. The window can be constructed to be very small diameters, into scale regimes in the order of visible light and even x-ray photonic wavelengths. FIG. 12 is a conceptual illustration that depicts a lens window 55 disproportionately large and not to scale with the rest of the lens assembly.

Referring to FIG. 10, the sensitivity profile of the lens is determined by the ratio of o to a and the absorptive ability of the cladding. FIG. 10 is a detailed diagram of the lens window 55 illustrating the geometric relationship of the angle of the reflected light 57 and the ability of the window 55 to discriminate non perpendicularly incident light.

In a variant, the window 55 comprises Schott Optical Glass, Designation B270 (or equivalent). The cladding 60 glass surrounding the widow may comprise Kimble Optical Glass, Designation R6 (or equivalent). The bulk glass 50 may comprise opaque Sem-Com Black Glass, Designation SCD-1 (or equivalent).

Figure 13:
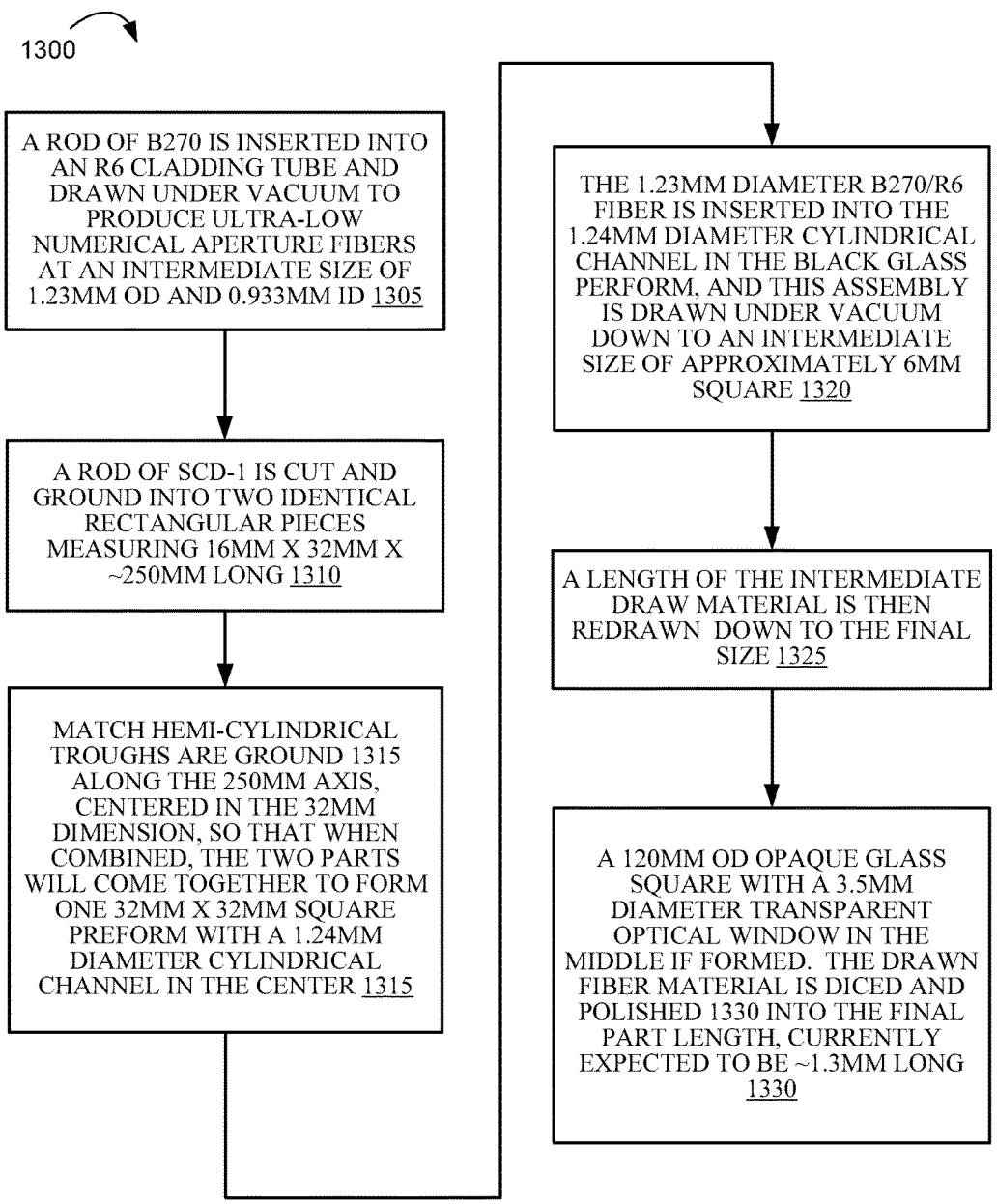
FIG. 13 is a flow chart of a process of manufacturing a lens for operation in the imaging system.

In another variant, referring to FIG. 13, a process 1300 for manufacturing the lens comprises the following: In a step 1305, a rod of B270 is inserted into an R6 cladding tube and drawn under vacuum to produce ultra-low numerical aperture fibers at an intermediate size of 1.23 mm OD and 0.933 mm ID (that is, the diameter of the B270 glass that was inside the cladding.). The eventual cut length of the fiber is variable. A rod of SCD-1 is cut 1310 and ground into two identical rectangular pieces measuring 16 mm×32 mm×~250 mm long. Referring to FIG. 16, matching hemi-cylindrical troughs are ground 1315 along the 250 mm axis, centered in the 32 mm dimension, so that when combined, the two parts will come together to form one 32 mm×32 mm square with a 1.24 mm diameter cylindrical channel in the center. Components shown in FIG. 16 are not drawn to scale relative to one another, for illustrative purposes. The 1.23 mm diameter B270/R6 fiber is inserted 1320 into the 1.24 mm diameter cylindrical channel in the black glass, and this assembly is drawn under vacuum down to an intermediate size of approximately 6 mm sq. A length of the intermediate draw material is then redrawn 1325 down to the final size, for example, a 120 μm by 120 μm opaque glass square with a 3.5 μm diameter transparent optical window in the middle. The drawn fiber material is diced and polished 1330 and cut into the final part length, for example, 1.3 mm long.

When the above process 1300 was carried out, the window that resulted exhibited excellent optical properties with excellent transmission of light through the length of the window and excellent selectivity for light entering parallel to the longitudinal axis of the window while filtering out light entering from other angles. In view of a comparative example (see below) which did not function, the properties observed for this example were surprisingly good. It was expected that the use of a cladding with a very slightly higher refractive index would have produced a superior window since only the parallel light and that light incident at very large angles would be transmitted through the total internal reflection property of fiberoptics; however, this is not what we found. In the case of the cladding with the higher refractive index, no light was transmitted. It is hypothesized that this result could have occurred because some diffusion occurs between the core fiber and the cladding glass and this caused even the parallel light to diffuse out of the fiber. Whether or not this hypothesis is correct; the observed result—that the use of a cladding with a slightly lower refractive index produced superior results, was a surprising finding that was contrary to the initial expectation.

The terms B270, R6, and SCD-1 refer to well-known glasses. B270 and R6 are highly transparent (>99% transparent to visible light), while SCD-1 is opaque. The B270 glass used in this example had a refractive index of 1.520 and the R6 had a refractive index of 1.517.

In a comparative example of synthesis of a window, a window was prepared according to the process 1300 described above, except that the cladding glass had a slightly higher refractive index as compared to the core glass. The resulting window was tested and it was found that this window did not transmit light.

To function as a lens that is selective for light rays that enter parallel to the longitudinal axis of the window and only those that are defined by the geometric characteristics of the light acceptance cone described by the length to diameter aspect of the window, the cladding should have a refractive index that is slightly less than the refractive index of the inner glass. In a preferred embodiment, the cladding has a refractive index that is no more than 0.030 less than that of the core glass and preferably no less than 0.010 less than that of the core glass. In some embodiments, the cladding may be between 0.001 and 0.007 less. In some embodiments the cladding is between 0.001 and 0.004 less.

Critical properties of the window in an intravascular catheter based imaging system are: (1) selectivity for the incident light that is parallel to the long axis of the window (ultra-low numerical aperture) and (2) efficiency (low loss) of transmission of that light through the window. A constant diameter of the window over its length is also desired so as to best achieve (1).

The transparent core of the window preferably has a diameter in the range of 0.1 to 10 μm that is variable dependent on application and is absolutely constant over the length of the fiber. The fiber comprising the transparent core and transparent cladding preferably has a thickness in the range of 0.001 to 0.1 μm; more preferably 0.001 μm. The width dimension of the opaque housing for the optical fiber is not critical, and in some embodiments is in the range of 25 μm to 1 mm. In preferred embodiments, the opaque housing has a square cross-section. The length of the window is preferably in the range of 500 to 1500 μm.

The window can be operated in this and other machines as both a light receiving discriminator and as a light illumination guide for emitting light, just as any optical lens may operate.

Figure 14:
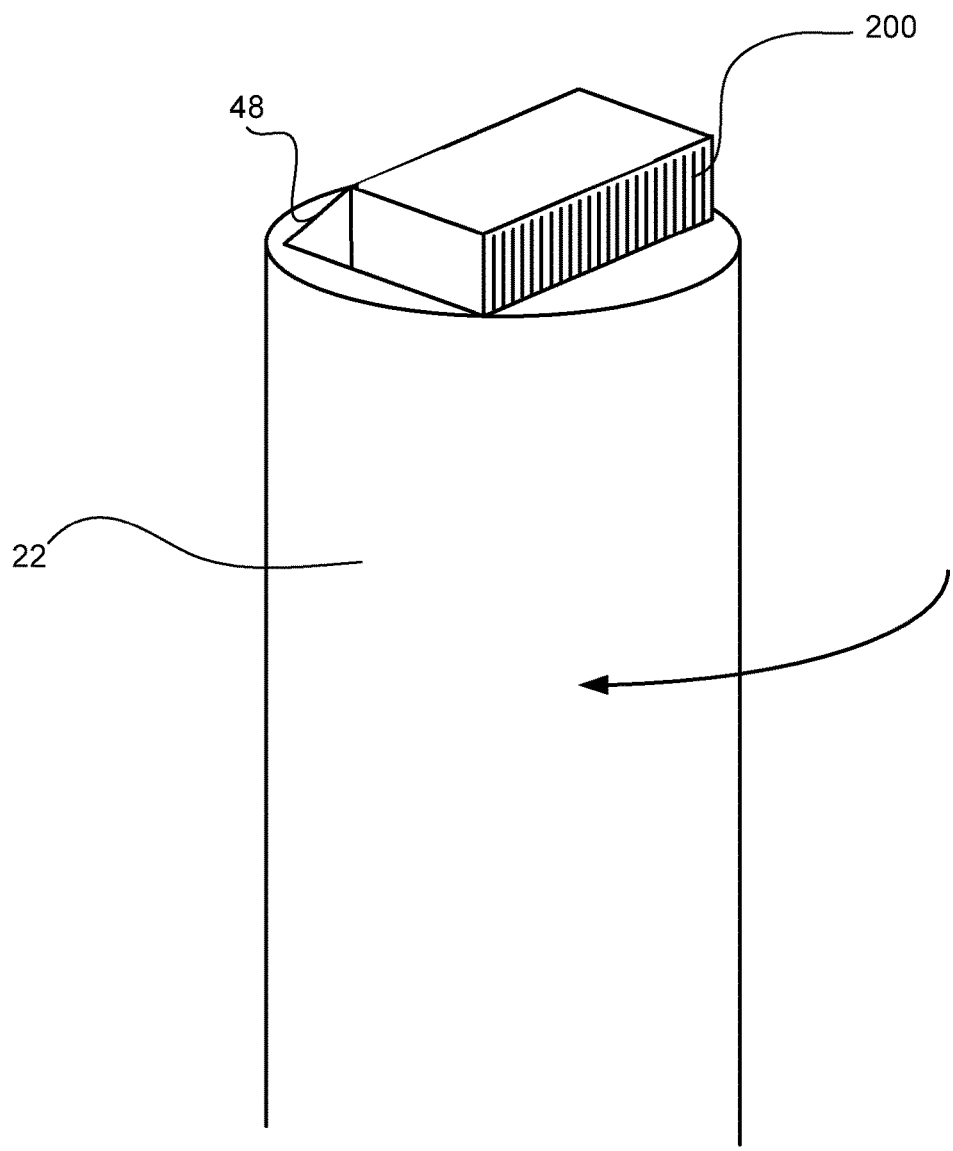
FIG. 14 is a perspective view of a rotating fiber having a nonoscale slit array functioning as a directional light discriminator.

In another variant, referring to FIG. 14, the lens is constructed of a nanoscale slit array 200 that is configured to have an acceptance zone that comprises a long and narrow ellipsoid like shape that is micron scale in its transverse profile, which defines the pixel size. An additional feature of this lens system is polarization of the accepted light. This polarization is utilized for multiplex signal transmission and thereby allows a very efficient design of an optical lens array system with fiber optic transmission of the imaging data via a single fiber to the decoding optics and photonic sensor system.

In a further variant, the lens system comprises a graded index fiber lens with characteristics of focusing the acceptance angle to a very narrow regime. In some embodiments, the acceptance angle is a cylinder of micron scale diameter.

In still another variant, the lens system is comprised of a CCD or CMOS small photonic sensor array coupled to a geometric optical sampling system including single pixel lenses and, optional mirrors that are optimized for the anatomy of interest. This miniaturized optional catadioptric optical sensor system may be engineered to have sufficient resolution and some variants require the use of a linear, ring, annular or spiral CMOS arrays due to the electronic advantages of these geometric sensor configurations. The optical sensor system may be utilized in a computational manner to generate perspective views.

Continuing with FIG. 2, in another variant, light emerging from the lens 30 enters a prism 48 connected to the lens. The prism redirects the captured light into a rotating fiber optic light guide 22 or rotor fiber, housed within the optical light tube 18. In a variant, the light is redirected by 90 degrees, the prism being shaped like a 45/90/45 triangle in cross section and having a reflective coating on its hypotenuse. The function of the prism 48 in this embodiment is to serve as a reflector, and not as a light separator. The rotating fiber optic light guide 22 leads into a fiber optic rotary adapter (FORA) having a rotor and stator subunits and a fiber optic rotary joint (FORJ) configured to join a rotating fiber optic light guide carrying light into a non-rotating fiber optic light guide with minimal loss. The FORA may optionally be configured to handle multichannel applications. Downstream of the FORA, the fiber optic light guide 20 leads to an analyzer 40.

Referring to FIG. 21, a process 2100 for forming a prism comprises the following: A rod or slab of glass for example, Schott Optical Glass, Designation F2 (or equivalent), is cut, ground, and polished 2105 into a 45/45/90 degree triangular cross-section, measuring approximately 25 inches on a side. The prism preform is drawn 2110 down to a target size of 0.12 mm on a side. The drawn material is diced 2115 into segments measuring approximately 0.12 mm long, producing prisms with 0.12×~0.12 mm input and output faces.

Other Imaging System Components

Figure 6:
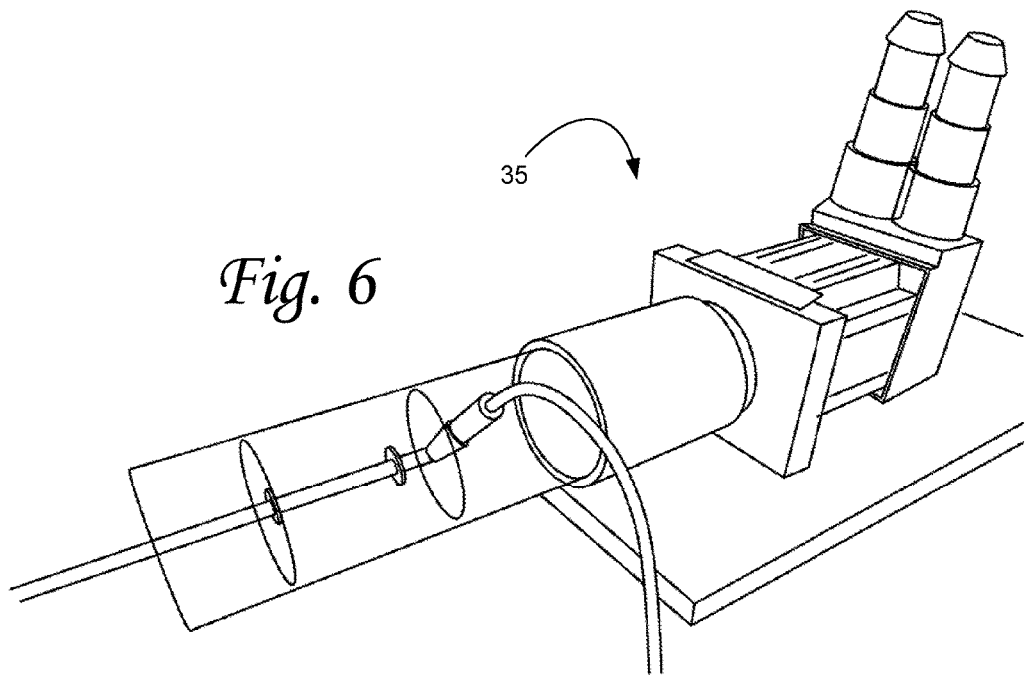
FIG. 6 is a perspective view of a drive mechanism.
Figure 7:
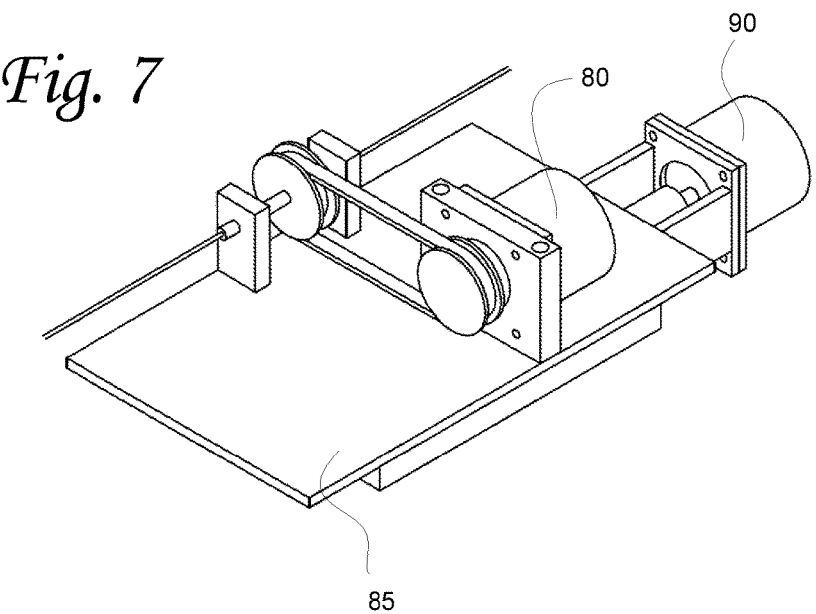
FIG. 7 is a perspective detail view of a drive mechanism.

A drive mechanism 35 is configured to move the lens assembly along the Z direction and rotate the lens assembly. In a variant, referring to FIGS. 6 and 7, the drive mechanism may comprise a rotating drive motor 80 set on a stage 85 connected to a second translating drive motor 90. The optical light tube 18 and the rotating fiber optic light guide 22 are connected to the translating drive motor 90 for translating both in unison along the Z direction, however only the rotating fiber optic light guide 22 is connected to the rotating drive motor 90, enabling the rotating fiber optic light guide 22 and components 30, 48 connected to it to rotate and translate along Z while the optical light tube 18 and components 20, 25 connected to it to only translate along Z.

In a variant, the analyzer 40 comprises a wavelength division multiplexer (WDM) or a band separating prism 54, a set of photo multiplier tubes 56, a processor (CPU) 65, an analog to digital converter (ADC) 70 and a reconstruction algorithm 75. The wavelength division multiplexer is configured for separating blue, red, green and IR wavelengths from the reflected light, and delivering them into respective light guides which lead to respective blue, red, green and IR photomultiplier tubes (PMT) 56. The PMTs are configured to convert the light received into a corresponding electrical signal dependent upon the intensity of the input light. The signals from the PMTs are fed into the ADC 70 for digitization which then sends the signal to the CPU 65 for processing. A reconstruction algorithm 75 accepts the digital output from the ADC 70 and generates a visible image of the vessel wall being imaged.

Given a capillary windows 30 (selective window) between 5.0 and 3.5 microns in width, the range of rotational speeds under ideal operating conditions (for example, about a 4 second acquisition time) may be between 500 RPS to 750 RPS, respectively. Without oversampling or the ADC/PMT limitations, this corresponds to approximately 419,000 cps and 942,000 cps, which generate 1.7 MP and 3.8 MP images, respectively, of an average carotid artery (flat scanned region 60 mm×25 mm). In this example, a preferred range for light capture events is between 400,000-3,200,000,000 cps.

Data from the PMT is segmented by the analog to digital converter (ADC) in order to send the data into a computer. The higher the bandwidth of the ADC device, the better the theoretical resolution of the system (the single pixel frame rate). Higher frame rates relate to the speed of acquisition of the image and the resolution of the image (through noise reduction via oversampling and averaging). A typical operational limit of a currently available ADC is about 3.2 gigahertz (same as for CPU's), which represents the highest number of light captures per second. In a variant, illumination may be performed using the lens 30 simultaneous to data acquisition, wherein the detected signal is different from the illumination signal due to different wavelengths, for example, in a fluorescence applications.

In another variant, a second rotating fiber optic light guide may be carried to the catheter tip.

In yet a further variant, a rotating fiber optic light guide is divided into hemicircular cross section light guides. Optionally circular cross section independent light guides are embedded into a circular cross-section composite rotor.

In still another variant, a focused and mixed laser sequentially targets regions of the light diffuser reflector. In non-flexible probes, such as brain parenchymal placements, this may be the optimal manner to illuminate. In non-flexible placements, the diffuser conduit is carried to the hub and extra-anatomic position of the probe. The annulus of the diffuser can accept a rotating laser guide to target specific areas of the reflector to provide directional illumination.

Figure 17:
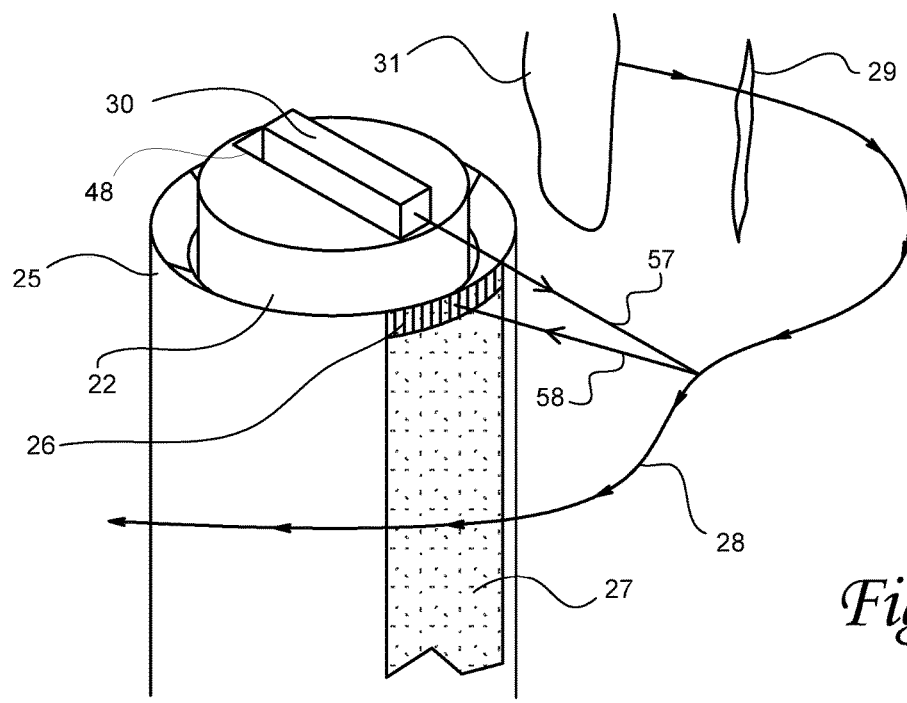
FIG. 17 is a perspective view of components of a variant of the imaging system, wherein light is emitted from a capillary lens and reflected light is detected by a channel of a light diffuser.
Figure 18:
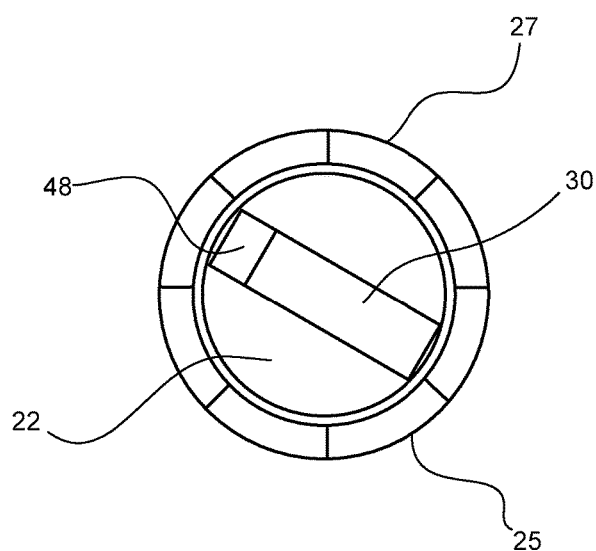
FIG. 18 is a top view of optical imaging components disposed in a catheter tip of the imaging system.

In a further variant, referring to FIG. 17, light, which may be laser light or coherent light or white light, or blended in other combinations, may be delivered to the lens 30 for emitting illumination light from the window directed at the vessel wall. The light diffuser 25 is then configured to detect reflected light impinging the a sensitive input area 26 on one of, for example eight, channels 27 which are independent light conduits that provide some directional discrimination by virtue of each one's limited extent on the diffuser 25. The focal spot of the laser light determines the resolution of the imaging system. The diffuser may have some directional discrimination of detected light, for example, 45 degrees of directional discrimination. The diffuser may have a plurality of independent optical channels for light detection. The lens 30 traces a path 28 along a surface of interest being imaged, which might reveal a tear 29 or an ulcer 31 when the image is reconstructed.

Reconstruction Methods

Figure 15:
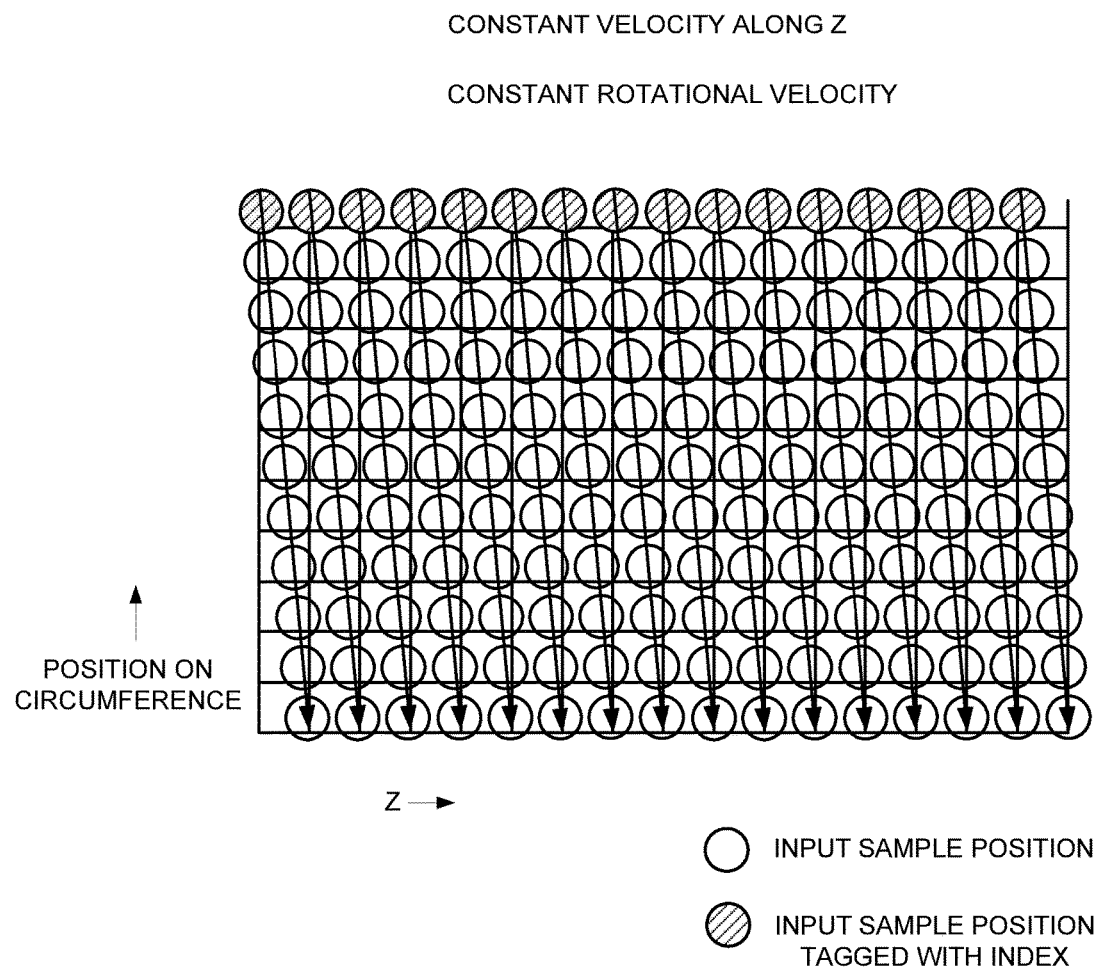
FIG. 15 is a conceptual diagram of a 2D reconstruction grid illustrating the relationship of the movement of a lens window through space and pixel data acquisition.

In a variant, referring to FIG. 4, the lens system 30 mounted onto the tip of the catheter, acquires image samples comprising color data, of the artery wall as it rotates around and translates along the central axis of the catheter. Given the large field of view and a high sampling rate of the lens system, computational algorithms reconstruct the image of the arterial wall. One of such algorithms 75 is illustrated in FIGS. 5 and 15. A 2-D image representation of the curved inner wall of a vessel is reconstructed by tiling each frame (pixel) 105, comprising light data acquired from the lens 30 and converted into digital signals via component, onto a standard rectangular grid of square pixels. The Z axis represents the translational distance traveled by the lens system along the central axis of the catheter. The Y axis represents the circumference of the lumen of an arterial wall or other vessel being imaged. Arrows 110 that transverse the graph illustrate the spiral motion of the lens system in space and in time. Each square within the figure represents an individual single pixel image sampled by the lens system. The exact units of the Z-Y axis are calibrated and determined by the spatial and temporal resolutions of the lens system in real time action.

Optionally, the drive mechanism is configured with a PID controller operable for maintaining constant rotational velocity and constant velocity in Z. Data points on the reconstructed image with a constant Z value represent all data obtained from light reflections from one particular ring of the vessel. Registration comprises alignment of consecutive circumferences, without misplacing pixels in an incorrect circumference. With known velocity in Z and rotational velocity, registration may be performed.

By knowing the velocity of the sensor, and the sampling rate (which is the number events detected by the lens and recorded by the system in a given unit of time), a readily calculated number of samples are expected to be obtained during each revolution of the lens. This is idealized registration. Optionally, the system may be configured for oversampling comprising repeated samples obtained at a given Z value for a ring. The samples for a given pixel are then averaged.

Idealized registration assumes perfect agreement between actual velocity and commanded velocity (and actual sample rate and commanded rate). Though both velocity and sample rate are highly accurate, they are not perfect, nor is this calculated value likely to be integral. For example, any constant imperfection will cause a precession of the rows seen as a skewing, or square rhombus on the image.

In a variant, if an item with a known geometry is imaged during acquisition of an image, the imaged item can be used to empirically correct skewing. For example, a test image containing a grid, or a guide wire extending into the field of view. For example, if a guide wire is in the field of view of the image inside the vessel, defects in the image are corrected by observing discontinuity in the image of the guide wire. A displaced section of the guide wire in the image, would indicate that the pixels should be shifted to properly align the image.

In another variant, an index signal is generated by the drive mechanism at the start point of every revolution of the lens system. Sample data acquired at the index position is tagged during each rotation, for example, as illustrated in FIG. 15. This registration information is independent of the field being sampled, allows any skewing to be corrected via software, and the ability to orient the image obtained to the real world position of the index signal.

In a further variant, the system is configured for prospective ECG gating of data acquisition by controlling the drive mechanism and ignoring data received during the off period of the gating during systole. Optionally, the motion of the drive mechanism is started and stopped in the Z direction while the angular velocity remains nonzero.

In some embodiments of the present invention, a portion of the illuminating light, typically in the longer wavelength, can be utilized to obtain adjunctive optical coherence tomographic (OCT) data via methods well known by those versed in this technique. The OCT data can be used to calculate the distance from the lens system to the arterial wall, and to provide tissue characterization of the arterial wall beneath its visible reflective surface. The core operating parameters of the lens system, such as the distance to the arterial wall, the angular velocity, the axial velocity, and the sampling rate can be used to superimpose a 2-D surface color rendering of the arterial wall (FIG. 5) onto a 3D image of the vessel for a more comprehensive visualization and examination.

Further reconstruction methods include a 3D radiographic angiogram incorporating the endolumenal optical image data. In this technique, a 3-D rotational angiogram is obtained with the imaging catheter in the target vessel of interest. A simultaneous or nearly simultaneous acquisition of the 3D angiogram and the endolumenal image is then obtained. The computational datasets can be combined to provide a very detailed 3D surface rendering of optical and surface topographic characteristics of the interior vessel surface.

Operation

In some variants, the catheter imaging system is configured to obtain an optical image using visible and optionally nonvisible light that is reflected or emitted from the surface of a tissue into which the imaging system is placed. In intravascular tissues, the blood pool may be cleared from the field using a standard radiographic contrast material that is optically transparent. Using a parallel full spectrum visible light source, a microscopic scale (on the order of 0.1-50 microns) image is acquired using a lens assembly.

Optionally the system of the present invention may be used in intravascular, intrabiliary placements using a standard or modified Seldinger technique. The catheter is positioned following standard fluoroscopically guided placement of a guidewire across the region of interest. Using radiographic markers built into the imaging catheter that indicate the imaging zone, the operator can position the device.

Optionally the imaging system may be placed in tissue using a standard Trocar technique, or, a hybrid of Trocar/Seldinger technique using facial dilators to separate tissue, and possibly a peel away type sheath to hold tissue in a retracted position, and allow atraumatic introduction of the imaging length of the catheter into the soft tissues (e.g. brain, liver).

Optionally the imaging system may be positioned through surgical ports and into surgically created spaces for use in manners similar to a traditional optical endoscope.

In another variant, the system may be configured to image distant objects. The system in the variant utilizes ambient light and detects reflected light through the lens 30. For example, the field of view may comprise a plane. The lens 30 is translated in two non parallel linear directions, for example x and y.

Variants of the imaging system are configured for far field microscopy from a remote imaging location at a catheter tip that is placed within a living organism. The catheter tip to target surface distance is variable due to the limitations inherent in catheter tip placement. In typical endovascular placements, a catheter and guidewire technique for placement may be utilized. In this situation, the catheter tip mounted imaging system will likely not be in the central vascular lumen during operation. Rather, it may be eccentrically located relative to an imaginary centerline of the vessel.

In another variant, the present invention provides an optical imaging catheter of sufficient resolution and sensitivity to enable research into the cell surface molecules and cell surface receptors as well as extracellular matrix elements that are important in atherosclerosis. Through the design and blood pool application of fluorescent reporter molecules, the spatial distribution of probe binding relative to anatomical locations of disease or other physiology could be directly studied in a nondestructive manner. This sort of study of this important disease may lead to a better understanding of the underlying disease process and could lead to improved medical treatments for atherosclerosis in the future including pharmaceutical and endovascular prosthesis development.

In other variants, the optical imaging system may be disposed directly into tissues of the body for in situ organ/tissue based fluorescence microscopy. In this manner, fluorescent reporter probes may be directly applied to the surrounding tissues, or, they may be administered in other manners. The optical imaging system will then be utilized to obtain physiological and pathophysiological data which may be used to inform pharmaceutical and endoprosthesis development.

Although the catheter described herein has mainly illustrated only imaging components, other lumens maybe employed within a catheter containing the imaging tip, which may be used also simultaneously for infusion or balloon inflation, during imaging.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. An imaging system, comprising:
   a light generating system;
   a fiber optic cable for propagating light generated by the light generating system;
   a means for redirecting light propagated by the fiber optic cable into a direction of an object to be imaged;
   a directional light discriminator configured for capturing light reflected from the object incident on a window of the discriminator from a particular direction and transmitting only the light captured from the particular direction to a second fiber optic cable or into the same first fiber optic cable carrying a net signal that corresponds to multiple wavelengths of light, wherein the directional light discriminator comprises a selective window, the selective window comprising:
   a transparent core having a first refractive index;
   a transparent cladding around the transparent core having a second refractive index; and
   an opaque housing around the cladding;
   wherein the second refractive index is between 0.001 and 0.030 less than the first refractive or is between 0.001 and 0.030 greater than the first refractive index;
   a drive motor coupled to the window, configured for sweeping the window through a plurality of directions in a pattern for matching each light capture event in the window with a direction of the window during the event;
   an optical to electrical conversion module configured for converting an optical signal corresponding to an light capture event into an electrical signal capable of being reconstructed into a visible image; and
   an optical light tube configured to receive a rotating optical light guide through a central bore, the optical light tube having channels distributed within a periphery of the optical light tube configured for receiving the fiber optic cable;
   an analyzer coupled to the fiber optic cable, configured to match the direction of the window with an associated light capture event and generate a visible image based on a mosaic of the captured light;
wherein the optical light tube is configured to translate in a linear direction while maintaining a fixed rotational position;
wherein the drive motor is configured to spin the directional light discriminator during light capture events; and
wherein the analyzer comprises a processor operable to reconstruct an image from reflected light data received from the directional light discriminator, by performing a reconstruction process comprising:
receiving rotation speed data of the directional light discriminator;
receiving light capture event rate data;
assigning a pixel value based on a signal generated by the light capture event;
assigning a first set of consecutive pixels to a first linear array based on the rotation speed data and the light capture event rate data;
assigning a second set of consecutive pixels to a second linear array adjacent to the first linear array based on the rotation speed data and the light capture event rate data; and
repeating the steps of assigning consecutive pixels to subsequent linear arrays based on the rotation speed data and the light capture event rate data.

2. The imaging system of claim 1, configured for deployment in interior body regions, further comprising a catheter tube, wherein the fiber optic cable, the directional light discriminator and the means for redirecting light propagated by the fiber optic cable are disposed inside the catheter tube and are configured to operate inside the catheter tube for imaging interior body regions.

3. The imaging system of claim 1, wherein the directional light discriminator comprises a single pixel camera.

4. The imaging system of claim 1, wherein the directional light discriminator comprises a channel formed of translucent material.

5. The imaging system of claim 1, wherein the directional light discriminator is configured having a geometric design that permits the passage of light through the discriminator only traveling from within an acceptance region in front of the discriminator determined by the geometry of the discriminator.

6. The imaging system of claim 1, wherein the directional light discriminator comprises a rotatable lens assembly, the lens assembly comprising a transparent channel surrounded by and held in place by a light absorbing material.

7. The imaging system of claim 1, further comprising an optical light tube configured to receive a rotating optical light guide through a central bore, the optical light tube having channels distributed within a periphery of the optical light tube configured for receiving the fiber optic cable;
wherein the optical light tube is configured to translate in a linear direction while maintaining a fixed rotational position.

8. The imaging system of claim 1, wherein the drive motor is configured to translate the directional light discriminator in a linear direction and rotate the directional light discriminator 360 degrees, allowing the directional light discriminator to capture reflected light emitted from the means for redirecting light propagated by the fiber optic cable and reflected off an object being imaged or capture induced fluorescently generated light, induced by illumination of light channeled by the means for redirecting light propagated by the fiber optic cable to the surface being imaged.

9. The imaging system of claim 1, wherein the light generating system comprises a laser for generating laser light; and
wherein the means for redirecting light propagated by the fiber optic cable comprises a light diffuser configured to combine light from one or more lasers and uniformly illuminate a region of space in front of the diffuser, the diffuser being connected to a fiber optic cable connected to the laser.

10. The imaging system of claim 1, further comprising a fiber optic rotary adaptor (FORA) comprising a rotor end and a stator end, the FORA connected downstream of the directional light discriminator, wherein the directional light discriminator is connected to the rotor end of the FORA via a rotating fiber optic light guide; and wherein the FORA is connected to the optical to electrical conversion module via a fiber optic light guide connected to the stator end.

11. The imaging system of claim 1, further comprising a light separator connected downstream of the directional light discriminator, wherein captured light from the directional light discriminator is divided into component light distinguished by wavelength by the light separator for processing by an analyzer.

12. The imaging system of claim 1, wherein the drive motor is configured to output an index signal to the processor at a constant point during each revolution of the directional light discriminator; wherein the processor is operable to:
assign the index signal to a pixel having a pixel value obtained from a light capture event occurring concurrently with the index signal; and
perform a check of the start pixels of the linear arrays with the pixels having assigned index signals.

13. The imaging system of claim 1, wherein the means for redirecting light propagated by the fiber optic cable is disposed adjacent the directional light discriminator and the means for redirecting light propagated by the fiber optic cable is configured to rotate in synchronicity with the directional light discriminator and illuminate the space in front both components.

14. The imaging system of claim 1, wherein the directional light discriminator comprises a nanoscale slit array.

15. A catheter based imaging system, configured for deployment in interior body regions, comprising:
a catheter tube;
a laser;
a first light guide for propagating light generated by the laser;
an optical light tube configured to receive the first light guide in a perimeter section of the light tube and having a channel configured to receive a rotating second light guide while not rotating wherein the optical light tube is configured to translate in a linear direction while maintaining a fixed rotational position;
a light diffuser connected to the first light guide, configured to uniformly distribute the light generated by the laser, and translate in a linear direction through the catheter tube;
a rotatable lens assembly, comprising a transparent channel surrounded by and held in place by a light absorbing material, the rotatable lens assembly configured translate in a linear direction in sync with the light diffuser;
a rotatable second light guide connected to the rotatable lens assembly;

a drive motor connected to the rotatable second light guide, and configured to sweep the lens assembly through a plurality of directions within the catheter in a pattern for matching each light capture event in the transparent channel with a direction of the lens during the event, the drive motor being configured to translate the lens assembly in a linear direction and rotate the lens assembly, and the drive motor being configured to translate the light diffuser in a linear direction through the catheter tube;

a means for redirecting light propagated by the fiber optic cable into a direction of an object to be imaged;

a directional light discriminator configured for capturing light reflected from the object incident on a window of the discriminator from a particular direction and transmitting only the light captured from the particular direction to the fiber optic cable;

an optical to electrical conversion module for converting an optical signal corresponding to an light capture event into an electrical signal capable of being reconstructed into a visible image; and an analyzer coupled to the fiber optic cable, configured to match the direction of the window with an associated light capture event and generate a visible image based on a mosaic of the captured light;

wherein the drive motor is configured to spin the directional light discriminator during light capture events; and wherein the analyzer comprises a processor operable to reconstruct an image from reflected light data received from the directional light discriminator, by performing a reconstruction process comprising:

receiving rotation speed data of the directional light discriminator;

receiving light capture event rate data;

assigning a pixel value based on a signal generated by the light capture event;

assigning a first set of consecutive pixels to a first linear array based on the rotation speed data and the light capture event rate data;

assigning a second set of consecutive pixels to a second linear array adjacent to the first linear array based on the rotation speed data and the light capture event rate data; and repeating the steps of assigning consecutive pixels to subsequent linear arrays based on the rotation speed data and the light capture event rate data.

16. A catheter based imaging system of claim 15, further comprising a fiber optic rotary adaptor (FORA) comprising a rotor end and a stator end, the FORA connected downstream of the lens assembly, wherein the lens assembly is connected to the rotor end of the FORA via the rotating light guide;

wherein the FORA is connected to the analyzer via a light guide connected to the stator end; and wherein the optical to electrical conversion module comprises a photomultiplier tube.

* * * * *